(12) United States Patent
Tilly et al.

(10) Patent No.: US 9,267,111 B2
(45) Date of Patent: Feb. 23, 2016

(54) METHODS OF TREATING FEMALE SUBJECTS IN NEED OF IN VITRO FERTILIZATION

(75) Inventors: Jonathan L. Tilly, Windham, NH (US); Joshua Johnson, New Haven, CT (US)

(73) Assignee: The General Hospital Corporation, Boston, MA (US)

( * ) Notice: Subject to any disclaimer, the term of this patent is extended or adjusted under 35 U.S.C. 154(b) by 736 days.

(21) Appl. No.: 13/006,752

(22) Filed: Jan. 14, 2011

(65) Prior Publication Data

US 2012/0195861 A1   Aug. 2, 2012

Related U.S. Application Data

(63) Continuation of application No. 11/131,152, filed on May 17, 2005, now abandoned.

(60) Provisional application No. 60/572,222, filed on May 17, 2004, provisional application No. 60/586,641, filed on Jul. 9, 2004, provisional application No. 60/574,187, filed on May 24, 2004.

(51) Int. Cl.
  *C12P 21/06* (2006.01)
  *C12N 5/0735* (2010.01)
  *A61K 35/12* (2015.01)

(52) U.S. Cl.
  CPC ............... *C12N 5/0611* (2013.01); *C12P 21/06* (2013.01); *A61K 2035/124* (2013.01)

(58) Field of Classification Search
  CPC .................................................... C12P 21/06
  USPC .......................................................... 435/68.1
  See application file for complete search history.

(56) References Cited

U.S. PATENT DOCUMENTS

| | | | |
|---|---|---|---|
| 6,875,854 | B1 | 4/2005 | Castrillon |
| 7,955,846 | B2 | 6/2011 | Tilly et al. |
| 8,062,222 | B2 | 11/2011 | Dirtinger et al. |
| 8,642,329 | B2 | 2/2014 | Tilly et al. |
| 8,647,869 | B2 | 2/2014 | Tilly et al. |
| 2003/0134422 | A1 | 7/2003 | Sayre |
| 2005/0130302 | A1 | 6/2005 | Nakauchi et al. |
| 2006/0010508 | A1 | 1/2006 | Tilly et al. |
| 2006/0010509 | A1 | 1/2006 | Johnson et al. |
| 2006/0015961 | A1 | 1/2006 | Tilly et al. |
| 2008/0050347 | A1 | 2/2008 | Ichim |
| 2009/0111764 | A1 | 4/2009 | Hillis et al. |
| 2013/0052727 | A1 | 2/2013 | Tilly et al. |

FOREIGN PATENT DOCUMENTS

| | | |
|---|---|---|
| EP | 1233978 | 8/2002 |
| WO | WO 01/30980 | 5/2001 |
| WO | WO-01/30980 | 5/2001 |
| WO | WO0136445 | 5/2001 |
| WO | WO 2004/009758 | 7/2004 |
| WO | WO2005007687 | 1/2005 |
| WO | WO2005/113752 | 12/2005 |
| WO | WO2005/121321 | 12/2005 |
| WO | WO/2006/001938 | 1/2006 |
| WO | WO-2012/142500 | 10/2012 |

OTHER PUBLICATIONS

Declaration of Dr. Jonathan L. Tilly Under 37 C.F.R. §1.132 dated Aug. 7, 2008.
ISR/Written Opinion issued in PCT/US2005/017233, Feb. 26, 2007, The General Hospital Corp.
ISR/Written Opinion/IPRP issued in PCT/US2005/017221, Jul. 27, 2006, The General Hospital Corp.
ISR/Written Opinion/IPRP issued in PCT/US2005/017234, Aug. 10, 2006, The General Hospital Corp.
Supplementary Search Report issued in EP-05779982.7, Sep. 17, 2008, The General Hospital Corp.
Supplementary Search Report issued in EP-05783644.7, Sep. 23, 2008, The General Hospital Corp.
Supplementary Search Report issued in EP-05782697.6, Oct. 15, 2008, The General Hospital Corp.
International Preliminary Report on Patentability issued for PCT/US05/17233, Jul. 25, 2008, The General Hospital Corp.
International Preliminary Report on Patentability issued for PCT/US05/17234, Jul. 25, 2008, The General Hospital Corp.
Powell, K., Going Against the Grain, PloS Biol 2007; 5:e338 (doi:10.1371/journal.pbio.0050338).
Bazer FW., Strong science challenges conventional wisdom: new perspectives on ovarian biology. Reprod Biol Endocrinol 2004; 2:28.
Gougeon A., Neo-oogenesis in the postnatal ovary: fantasy or reality? Gynecol Obstet Fertil 2005; 33:819-823.
Kayisli UA et al., Stem cells and fertility: what does the future hold? Curr Opin Obstet Gynecol 2006; 18:338-343.
Faddy M. et al., Numbers of ovarian follicles and testing germ line renewal in the postnatal ovary. Facts and fallacies. Cell Cycle 2007; 6:1951-1952.
Oktem O. et al., Stem cells: a perspective on oocytes. Ann NY Acad Sci USA 2008; 1127:20-26.
Zuckerman S., Beyond the Ivory Tower. The Frontiers of Public and Private Science. New York: Taplinger; 1971:22-34.
Waldeyer W. Eierstock und Ei. Engelmann, Leipzig; 1870.
Zhang D et al., Expression of stem and germ cell markers within nonfollicle structures in adult mouse ovary. Reprod Sci 2008; 15:139-146.
Vermande-Van Eck G., Neo-ovogenesis in the adult monkey. Anat Rec 1956; 125:207-224.
Flaws JA, et al., Chronically elevated luteinizing hormone depletes primordial follicles in the mouse ovary. Biol Reprod 1997; 57:1233-1237.

(Continued)

*Primary Examiner* — Ardin Marschel
(74) *Attorney, Agent, or Firm* — Saul Ewing LLP; Peter C. Lauro, Esq.

(57) ABSTRACT

Described herein are methods of treating a female subject in need of in vitro fertilization to become pregnant by detecting a loss of non-atretic follicles in the female subject and providing in vitro fertilization to the female subject.

11 Claims, 8 Drawing Sheets

(56) References Cited

OTHER PUBLICATIONS

Dissen GA, et al., Romero C., Hirshfield AN, Ojeda SR. Nerve growth factor is required for early follicular development in the mammalian ovary. Endocrinology 2001; 142:2078-2086.

Nilsson EE, et al., Bone morphogenetic protein-4 acts as an ovarian follicle survival factor and promotes primordial follicle development. Biol Reprod 2003; 69:1265-1272.

Tomic D et al., Ovarian follicle development requires Smad3, Mol Endocrinol 2004; 18:2224-2240.

Rajkovia A et al., NOBOX deficiency disrupts early folliculogenesis and oocyte-specific gene expression. Science 2004; 305:1157-1159.

Castrillon DH et al., Suppression of ovarian follicle activation in mice by the transcription factor Foxo3a. Science 2004; 301:215-218.

Lohff JC et al., Effect of duration of dosing on onset of ovarian failure in a chemical-induced mouse model of perimenopause. Menopause 2006; 13:482-488.

Reddy P et al., Oocyte-specific deletion of Pten causes premature activation of the primordial follicle pool. Science 2008; 319:611-613.

Gosden RG. Ovarian support of pregnancy in ageing inbred mice. J Reprod Fertil 1975; 42:423-430.

Gosden RG. Effects of age and parity on the breeding potential of mice with one or two ovaries. J. Reprod Fertil 1979; 57:477-487.

Nelson JF et al., Effects of dietary restriction on estrous cyclicity and follicular reserves in aging C57BL/6Jmice. Biol Reprod 1985; 32:515-522.

Eichenlaub-Ritter U et al., The CBA mouse as a model for age-related aneuploidy in man: studies of oocyte maturation, spindle formation and chromosome alignment during meiosis. Chromosoma (Berl) 1988; 96:220-226.

Allen E. Ovogenesis during sexual maturity. Am J Anat 1923; 31:439-482.

Bucci LR et al., Effects of busulfan on murine spermatogenesis: cytotoxicity, sterility, sperm abnormalities and dominant lethal mutations. Mutat Res 1987; 176:259-268.

Brinster RL et al., Germline transmission of donor haplotype following spermatogonial transplantation. Proc Natl Acad Sci USA 1994; 91:11303-11307.

Ogawa T et al., Transplantation of testis germinal cells into mouse seminiferous tubules. Int J. Dev Biol 1997; 41:111-122.

Pelloux MC et al., Effects of busulphan on ovarian folliculogenesis, steroidogenesis and anti-Mullerian activity of rat neonates. Acta Endocrinol 1988; 118:218-226.

Perez GI et al., Apoptosis-associated signaling pathways are required for chemotherapy-mediated female germ cell destruction. Nat Med 1997; 3:1228-1232.

Perez GI et al., Fragmentation and death (a.k.a. apoptosis) of ovulated oocytes. Mol Hum Reprod 1999; 5:414-420.

Morita Y et al., Oocyte apoptosis is suppressed by disruption of the acid sphingomyelinase gene or by sphingosine-1-phosphate therapy. Nat Med 2000; 6:1109-1114.

Baltus AE et al., In germ cells of mouse embryonic ovaries, the decision to enter meiosis precedes premeiotic DNA replication. Nat Genet 2006; 38:1430-1434.

Zhou Q et al., Expression of stimulated by retinoic acid gene 8 (Stra8) and maturation of murine gonocytes and spermatogonia induced by retinoic acid in vitro. Biol Reprod 2008; 78:537-545.

Bowles J et al., Retinoic acid signaling determines germ cell fate in mice. Science 2006; 312:596-600.

Koubova J et al., Retinoic acid regulates sex-specific tijming of meiotic initiation in mice. Proc Natl Acad Sci USA 2006; 103:2474-2479.

Lee H-J et al., Loss of CABLES1, a cyclin-dependent kinase-interacting protein that inhibits cell cycle progression, results in germline expansion at the expense of oocyte quality in adult female mice. Cell Cycle 2007; 6:2678-2684.

Bristol-Gould SK et al., Postnatal regulation of germ cells by activin: the establishment of the initial follicle pool. Dev Biol 2006; 298:132-148.

Lin H. The stem-cell niche theory: lessons from flies. Nat Rev Genet 2002; 3:931-940.

Ogawa T et al., The niche for spermatogonial stem cells in the mammalian testis. Int. J. Hematol 2005; 82: 381-388.

Bukovsky A et al., Origin of germ cells and formation of new primary follicles in adult human ovaries. Reprod Biol Endocrinol 2004; 2:28.

Bukovsky A et al., Oogenesis in cultures derived from adult human ovaries. Reprod Biol Endocrinol 2005; 3:17.

Bukovsky A et al., Mammalian neo-oogenesis and expression of meiosis-specific protein SCP3 in adult human and monkey ovaries. Cell Cycle 2008; 7:683-686.

Bristol-Gould SK et al., Fate of the initial follicle pool: empirical and mathematical evidence supporting its sufficiency for adult fertility. Dev Biol 2006; 298:149-154.

Peters H. The development of the mouse ovary from birth to maturity. Acta Endocrinol 1969; 62:98-116.

Elvin JA et al., Molecular characterization of the follicle defects in the growth differentiation factor 9-deficient ovary. Mol Endocrinol 1999; 13: 1018-1034.

Myers M et al., Methods for quantifyying follicular numbers within the mouse ovary. Reproduction 2004; 127:569-580.

Huntriss J et al., cDNA cloning and expression of the human NOBOX gene in oocytes and ovarian follicles. Mol Hum Reprod 2006; 12:283-289.

John GN et al., Specificity of the requirement for Foxo3 in primordial follicle activation. Reproduction 2007; 133:855-863.

Ohta H et al., Commitment of fetal male germ cells to spermatogonial stem cells during mouse embryonic development. Biol Reprod 2004; 70:1286-1291.

Hubner K et al., Derivation of oocytes from mouse embryonic stem cells. Science 2003; 300:1251-1256.

Novak I et al., Mouse embryonic stem cells form follicle-like ovarian structures but do not progress through meiosis. Stem Cells 2006; 8:1931-1936.

Kerkis A et al., In vitro differentiation of male mouse embryonic stem cells into both presumptive sperm cells and oocytes. Cloning Stem Cells 2007; 9:535-548.

Nagano MC. In vitro gamete derivation from pluripotent stem cells: progress and perspective. Biol Reprod 2007; 76:546-551.

Dyce PW et al., In vitro germline potential of stem cells derived from fetal porcine skin. Nat Cell Biol 2006; 8:384-390.

Dyce PW et al., From skin cells to ovarian follicles? Cell Cycle 2006; 5:1371-1375.

Danner S et al., Derivation of oocyte-like cells from a clonal pancreatic stem cell line. Mol Hum Reprod 2007; 13:11-20.

Toyooka Y et al., Embryonic stem cells can form germ cells in vitro. Proc Natl Acad Sci USA 2003; 100:11457-11462.

Geijsen N et al., Derivation of embryonic germ cells and male gametes from embryonic stem cells. Nature 2004; 427:148-154.

Lue Y et al., Fate of bone marrow stem cells transplanted into the the testis: implications for men with testicular failure. Am J Pathol 2007; 170;899-908.

Drusenheimer N et al., Putative human male germ cells from bone marrow stem cells. Soc Reprod Fertil Suppl 2007; 63:69-76.

Yeom YI et al., Germline regulatory element of Oct-4 specific for the totipotent cycle of embryonal cells. Development 122:881-894, (1996).

Yoshimizu T et al., Germline-specific expression of the Oct-4/green fluorescent protein (GFP) transgene in mice. Dev Growth Differ 1999; 41:675-684.

Szabo PE et al., Allele-specific expression of imprinted genes in mouse migratory primordial germ cells. Mech Dev 2002; 115:157-160.

Begum S et al., The oocyte population is not renewed in transplanted or irradiated adult ovaries. Hum Reprod 2008; (doi:10.1093/humrep/den249).

Fu X et al., Bone marrow mesenchymal stem cell transplanation improves ovarian function and structure in rats with chemotherapy-induced damage. Cytotherapy 2008; 10:353-363.

Tilly JL et al., Stem cell contribution to ovarian development, function and disease. Endocrinology 2008; (doi:10.1210/en.2008-0458).

(56) References Cited

OTHER PUBLICATIONS

Shankle WR et al., Evidence for a postnatal doubling of neuron number in the developing human cerebral cortex between 15 months and 6 years. J Theor Biol 1998; 191:115-140.
Shankle WR et al., Approximate doubling of number of neurons in postnatal human cerebral cortex and in 35 specific cytoarchitectural areas from birth to 72 months. Pediatr Dev Pathol 1999; 2:244-259.
Gould E et al., Neurogenesis in the neocortex of adult primates. Science 1999; 286:548-552.
Korr H et al., Facts and fictions regarding post-natal neurogenesis in the developing human cerebral cortex. J Theor Biol 1999; 200:291-297.
Nowakowski RS et al., New Neurons: extraordinary evidence or extraordinary conclusion? Science 2000; 288:771a.
Rakic P. Neurogenesis in the adult primate neocortex: an evaluation of the evidence. Nat Rev Neurosci 2002; 3:65-71.
Blakeslee S. A decade of discovery yields a shock about the brain. New York Times 2000 (Jan.); F1, F4.
Gross CG. Neurogenesis in the adult brain: death of a dogma. Nat Rev Neurosci 2000; 1:67-73.
Gould E et al., Adult-generated hippocampal and neocortical neurons in macaques have a transient existence. Proc Natl Acad Sci USA 2001; 98: 10910-10917.
Gould E et al., Neurogenesis in adult mammals: some progress and problems. J Neurosci 2002; 22:619-623.
Leuner B et al., Diminished neurogenesis in the marmoset brain precedes old age. Proc Natl Acad Sci USA 2007; 104:17169-17173.
Revishchin AV et al., Neural stem cells in the mammalian brain. Int Rev Cytol 2008; 265-55-109.
Maurer MH et al., Screening the brain: molecular fingerprints of neural stem cells. Curr Stem Cell Res Ther 2006; 1:65-77.
Taupin P. Therapeutic potential of adult neural stem cells. Rec Patents CNS Drug Discov 2006; 1:299-303.
Beaumont HM et al., A quantitative and cytological study of oogonia and oocytes in the fetal and neonatal rat. Proc R Soc Lond B 1961; 155:557-579.
Baker TG et al., The fine structure of oogonia and oocytes in human ovaries. J Cell Sci 1967; 2:213-224.
Gosden RG. Follicular status at menopause. Hum Reprod 1987; 2:617-621.
Selesniemi K et al., Moderate caloric restriction initiated in rodents during adulthood sustains function of the female reproductive axis into advanced chronological age. Aging Cell 2008; (doi:10.1111/j.1474-9726.2008.00409.x).
Perez GI et al., Absence of the pro-apoptotic Bax protein extends fertility and alleviates age-related health complications in female mice. Proc Natl Acad Sci USE 2007; 104: 5229-5234.
Kirilly D et al., The *Drosophila* ovary: an active stem cell community. Cell Res 2007; 17:15-25.
Pearl R et al., Studies on the physiology of reproduction in the domestic fowl. J Exp Zool 1921; 34:101-118.
Underwood JL et al., Gonad regeneration in grass carp following bilateral gonadectomy. Progressive Fish-Culturist 1986; 48:54-56.
Draper BW et al., nanos1 is required to maintain oocyte production in adult zebrafish. Dev Biol 2007; 305:589-598.
Salooja N et al., Successful pregnancies in women following single autotransplant for acute myeloid leukemia with a chemotherapy ablation protocol. Bone Marrow Transplant 1994; 13:431-435.
Socie G et al., Late Effects Working Party of the European Study Group for Blood and Marrow Transplantation. Nonmalignant late effects after allogeneic stem cell transplantation. Blood 2003; 101:3373-3385.
Oktay K et al., Regeneration of oocytes after chemotherapy: connecting the evidence from mouse to human. J. Clin Oncol 2007; 25:3185-3187.
Tropel P et al., Isolation and Characterization of Mesenchymal Stem Cells from Adult Mouse Bone Marow. Experimental Cell Research, May 1, 2004. 295(2); 395-406.

Logothetou-Rella "Description of primordial germ cells, oogonia, oocytes and embryo-like growth in squash preparations of issues from hematological malignancies" Histology and Histopathology 11: 965-984 (1996).
Nayernia et al. "Derivation of male germ cells from bone marrow stem cells" Lab Invest. 86(7): 654-663 (2006).
Johnson et al. "Oocyte Generation in Adult Mammalian Ovaries by Putative Germ Cells in Bone Marrow and Peripheral Blood" Cell 122: 303-315 (2005).
Kucia et al. "A population of very small embryonic-like (VSEL) CZCR4+SSEA-1+ Oct-4+ Stem cells identified in adult bone marrow" Luekemia 20: 857-869 (2006).
Pochampally et al. "Serum deprivation of human marrow stromal cells (hMSCs) selects for a subpopulation of early progenitor cells with enhanced expression of OCT-4 and other embryonic genes" Blood 103(5): 1647-1652 (2004).
Hayashi et al. "Mouse preimplantation Embryos Developed from Oocytes Injected with Round Spermatids or Spermatozoa Have Similar but Distinct Patterns of Early Messenger RNA Expression" Biology of Reproduction 69: 1170-1176 (2003).
Hovatta et al. "A culture system using human foreskin fibroblasts as feeder cells allows production of human embryonic stem cells" Human Reproduction 18(7): 1404-1409 (2003).
Bukovsky et al. "Potential new strategies for the treatment of ovarian infertility and degenerative diseases with autologous ovarian stem cells" Expert Opin. Biol. Ther. 6(4): 341-365 (2006).
Eggan et al. "Ovulated oocytes in adult mice derive from non-circulating germ cells." Nature 441; 1109-1114 (2006).
Anderson, Biol Reprod. 1988; 38(1) 1-15.
Decotto et al., Dev cell. 2005; 9(4): 501-10.
Gage, F., Nature 392: 18-24, 1998.
Goswami et al., 2005. Premature Ovarian Failure. Hum Reprod Update 11: 391-410.
Hildebrandt et al., 2000. Detection of Germ-cell Tumor Cells in Peripheral Blood Progenitor Cell Harvests: Impact on Clinical Outcome. Clin Cancer Res 6: 4641-4646.
Samstein et al., Journal of American Society of Nephrology 12: 182-193, 2001.
Virant-Klun et al., Stem Cells and Development, Jul. 2008 pp. 1-43.
Yamashita et al., Journal of Cell Science 118, 665-672, 2005.
Powell "Skeptics demand duplication of controversial fertility claim" Nat Med 11:911 (2005).
Powell "Born or made? Debate on mouse eggs reignites" Nature 441: 795 (2006).
Ainsworth "Bone cells linked to creation of fresh eggs in mammals" Nature 436: 609 (2005).
Greenfeld et al. "Renewed debate over postnatal oogenesis in the mammalian ovary" Bioessays 26:829-32 (2004).
Gosden "Germline stem cells in the postnatal ovary: is the ovary more like a testis?" Hum Reprod Update 10(3) 193-195 (2004).
Albertini "Micromanagement of the ovarian follicle reserve—do stem cells play into the ledger?" Reproduction 127: 513-514 (2004).
Vogel "Controversial study finds unexpected source of oocytes" Science 309: 678-679 (2005).
Hoyer Can the clock be turned back on ovarian aging? Sci Aging Knowledge Environ 10:pe11 (2004).
Telfer "Germline stem cells in the postnatal mammalian ovary: a phenomenon of prosimian primates and mice?" Reprod Biol Endocrinol 2:24 (2004).
Telfer et al. "On regenerating the ovary and generating controversy" Cell 122: 821-22 (2005).
Kerr et al. "Quantification of healthy follicles in the noenatal and adult mouse ovary: evidence for maintenance of primordial follicle supply" Reproduction 132: 95-109 (2006).
Skaznik et al. "Serious doubts over Eggs forever?" Differentiation 74: 1-7 (2006).
Salooja et al. "Late Effects of working party of the European Group for blood and marrow transplantataion. Pregnancy outcomes after peripheral blood or bone marrow transplantation: a retrospective study." Lancet 358: 271-276 (2001).

(56) References Cited

OTHER PUBLICATIONS

Samuelsson et al. "Successful pregnancy in a 28 year old patient autographed for acute lymphoblastic leukemia following myeloablative treatment including total body irradiation." Bone Marrow Transplant 12: 659-660 (1993).
Sanders et al. "Pregnancies following high-dose cyclophosphamide with or without high-dose busulfan or total-body irradiation and bone marrow transplantation." Blood 87: 3045-3052 (1996).
Johnson et al., "Germline stem cells and follicular renewal in the postnatal mammalian ovary." Nature 48(11):145-150 (2004).
Hershlag et al. "Return of fertility after autologous stem cell transplantation." Fertility and Sterility 77(2) 419-421 (2002).
Zhou, K, et al. "Production of Offspring from a Germline Stem Cell Line Derived from Neonatal Ovaries" Nature Cell Biology Online Publication, published online Apr. 12, 2009; DOI 10.1038/ncb1869, pp. 1-20.
Tropel et al., Isolation and Characterization of Mesenchymal Stem Cells from Adult Mouse Bone Marrow. Experimental Cell Research, May 1, 2004. 295(2); 395-406.
Wittstock et al., Analytical Biochemistry, 292, 166-169, 2001.
Castrillon et al., (PNAS, 97-17: 9585-9590, 2000).
Clark, et al., (Stem Cells, 22: 169-179, 2004).
Johnson et al., "Germline stem cells and follicular renewal in the postnatal mammalian ovary." Nature 428: 145-150 (2004).
Byskov et al. "Eggs forever?" Differentiation 73: 438-446 (2005).
Johnson et al. "Setting the Record Straight on Data Supporting Postnatal Oogenesis in Female Mammals" Cell Cycle 4:11, 14771-1477 (2005).
Logothetou-Rella Description of primordial germ cells, oogonia, oocytes and embryo-like growth in squash preparations of issues from hematological malignancies: Histology and Histopathology 11: 965-984(1996).
Logothetou-Rella "Meiosis in hematological malignancies. In situ cytogenetic morphology" Histology and Histopathology 11: 943-963 (1996).
Thomson et al., Science, 282: 1145-1147, 1998.
Clark et al., Human Molecular Genetics, 13(7): 727-739, 2004.
Reubinoff et al., Nature Biotechnology, 18: 399-404, 2000.
Lin et al., Stem Cells, 21: 152-161, 2003.
Gosden, Human Reproduction Update, 10(3): 193-195, 2004.
Bukovsky, et al., Reproductive Biology and Endocrinology, 2:20, 2004.
Spradling, Nature, 428: 133-134, 2004.
Balakier et al., "Morphological and Cytogenetic Analysis of Human Giant Oocytes and Giant Embryos" Human Reproduction 17(8): 2394-2401 (2002).
Sotile "Bone Marrow as a Source of Stem Cells and Germ Cells? Perspectives for Transplantation" Cell Tissue Res. 328:1-5 (2007).
Hua, Jinlian et al., Derivation of male germ cell-like lineage from human fetal bone marrow stem cells, Reproductive BioMedicine Online; www.rbmonline.com/Article/3742 on web May 8, 2009, vol. 19, No. 1. 2009-99-105.
Lovell-Badge, Robin, Banking on spermatogonial stem cells: Frozen assets and foreign investments, Nature Medicine, vol. 2, No. 6, Jun. 1996.
Meachem et al., Spermatogonia: stem cells with a great perspective, Reproduction (2001), 121, 825-834.
Nistal et al., Decrease in the Number of Human Ap and Ad Spermatogonia and in the Ap/Ad Ratio with Advancing Age, J Androl 1987; 8:64-68.
Paniagua et al., Quantification of cell types throughout the cycle of the human seminiferous epithelium and their DNA content, Anatomy and Embryology (1987) 176: 225-230.
Schulze, Cornelia, Response of the human testis to long-term estrogen treatment: Morphology of Sertoli cells, Leydig cells and spermatogonial stem cells, Cell and Tissue Research (1998) 251: 31-43.
Anderson "An overview of follicular development in the ovary: From embryo to the fertilized ovum in vitro." Md. Med. J. 41: 614-620 (1992).

Korbling et al. "Peripheral blood stem cell versus bone barrow allotransplantation: does the source of hematopoietic stemm cells matter?" Blood 98: 2900-2908 (2001).
Ho et al., "Hematopoietic stem cells: can old cells learn new tricks?" J Leukoc Biol 73: 547-555 (2003).
Sanchez-Ramos "Neural Cells Derived From Adult Bone Marrow and Umbilical Cord Blood." J Neurosci Res 69: 880-893 (2002).
Lee "Isolation of multipotent mesenchymal stem cells from umbilical cord blood." Blood 103:1669-75 (2004).
Rogers et al. "Lifeline in an Ethical Quagmire: Umbilical Cord Blood as an Alternative to Embryonic Stem Cells." Sexuality, Reproduction & Menopause 2: 64-70 (2004).
Green et al. "Do cells outside the testes participate in repopulating the germinal epithelium after irradiation?" Int. J. Radiat. Biol. vol. 17 (1): 87-92 (1970).
Morita et al. "Oocyte Apoptosis: Like Sand through an Hourglass" Dev. Biol. 213: 1-17 (1999).
Tilly, J.L., "Commuting the Death Sentence: How Oocytes Strive to Survive." Nat. Rev. Mol. Cell Biol. 2: 838-848 (2001).
Faddy et al., "The kinetics of pre-antral follicle development in ovaries of CBA/Ca mice during the first 14 weeks of life." Cell Tissue Kinet. 20: 551-560 (1987).
Faddy, M.J., "Follicle dynamics during ovarian ageing." Mol. Cell. Endocrinol. 163: 43-48 (2000).
Faddy et al., "An Analytical Model for Ovarian Follicle Dynamics." J. Exp. Zool. 197: 173-186 (1976).
Richardson et al. "Follicular Depletion During the Menopausal Transition: Evidence for Accelerated Loss and Ultimate Exhaustion." J. Clin. Endocrinol. Metab. 65: 1231-1237 (1987).
Borum "Oogenesis in the Mouse, A Study of the Meiotic Prophase." Exp. Cell Res. 24: 495-507 (1961).
McLaren "Meiosis and Differentiation of Mouse Germ Cells." Symp. Soc. Exp. Biol. 38: 7-23 (1984).
Peters "Migration of gonocytes into the mammalian gonad and their differentiation." Phil. Trans. R. Soc. Lond. B, 259: 91-101 (1970).
Waxman "Chemotherapy and the adult gonad: a review." J. R. Soc. Med. 76: 144-8 (1983).
Familiari et al., "Ultrastructure of human ovarian primordial follicles after combination chemotherapy for Hodgkin's disease." Hum. Reprod. 8: 2080-7 (1993).
Ried et al. "Radiation-Induced Changes in Long-Term Survivors of Childhood Cancer After Treatment with Radiation Therapy." Semin. Roentgenol. 29: 6-14 (1994).
Reichman et al. "Breast Cancer in Young Women: Effect of Chemotherapy on Ovarian Function, Fertility, and Birth Defects." J. Natl. Cancer Inst. Monogr. 16: 125-9 (1994).
Tilly "Recent Arguments Against Germ Cell Renewal in the Adult Human Ovary." Cell Cycle, 6:8, 879-883, (2007).
Veitia et al, "Recovery of Female Fertility After Chemotherapy, Irradiation, and Bone Marrow Allograft: Further Evidence Against Massive Oocyte Regeneration by Bone Marrow-Derived Germline Stem Cells." Stem Cells, DOI: 10.1634/stemcells.2006-0770 (2007).
Lee et al. "Bone Marrow Transplantation Generates Immature Oocytes and Rescues Long-Term Fertility in a Preclinical Mouse Model of Chemotherapy-Induced Premature Ovarian Failure." J Clin Oncol.; 25: 3198-3204 (2007).
Liu et al., "Germline stem cells and neo-oogenesis in the adult human ovary." Dev. Biol. (DOI: 10.1016/j.ydbio.2007.03.006 (2007).
Gougeon et al. "Regulation of Ovarian Follicular Development in Primates: Facts and Hypotheses." Endocr Rev. 17: 121-55 (1996).
Zuckerman "The Number of Oocytes in the mature Ovary." Recent Prog. Horm. Res. 6: 63-108 (1951).
Perez et al. Nature Genetics 21:200-203 (1999).
Fujiwara, et al., Isolation of a DEAD-family protein gene that encodes a murine homolog of Drosophila vasa and its specific expression in germ cell lineage, Proc. Natl. Acad. Sci. USA, vol. 91, pp. 12258-12262, Dec. 1994.
Pacchiarotti, et al., Differentiation Potential of Germ Line Stem Cells Derived from the Postnatal Mouse Ovary, International Society of Differentiation (2010), doi: 10.1016/j.diff.2010.01.001.
Ghadami et al., Intravenously Injected Bone Marrow Cells Restore Ovarian Folliculogenesis and Steroid Hormones Production in

(56) References Cited

OTHER PUBLICATIONS

Female FSHE (-1-) Mice. Reproductive Sciences, 15(1) (Supplement)—Abstract No. 597, Jan. 2008.
Virant-Klun, et al., Putative Stem Cells with an Embryonic Character Isolated from the Ovarian Surface Epithelium of Women with no Naturally Present Follicles and Oocytes. Differentiation, pp. 1-14, DOI: 10.111/j. 1432-0436.2008.00268.x Feb. 2008.
Webster's Ninth New Collegiate Dictionary, Merriam-Webster Inc., 2000, Springfield, MA (web excerpt—definition of "correspond").
Noce et al., Vasa homolog genes in mammalian germ cell development. Cell Struct Funct 26:131-136, 2001.
K. Zou, et al., "Production of Offspring from a Germline Stem Cell Line Derived from Neonatal Ovaries" Nature Cell Biology Advance Online Publication DOI:1038/ncb 1869: 1-20 (Apr. 12, 2009).
Zuckerman, Recent Prog Harm Res 1951; 6:63-109.
Johnson et al., Nature 2004; 428:145-150.
Spradling, *Nature* 2004 428:133-134.
Johnson et al., Cell 2005; 122:303-315.
Ventura *Vital Health Stat* 47:1-27, 1989.
Henderson et al., *Nature* 218:22-28, 1968.
Hassold et al., *Hum Genet* 70:11-17, 1985.
Battaglia et al., *Hum Reprod* 11:2217-2222, 1996.
Tarin et al., *Mol Reprod Dev* 61 :385-397, 2002.
Tarin et al., *Theriogenology* 57:1539-1550, 2002.
Bartmann et al., J Assist Reprod Genet 2004; 21:79-83.
Wilding et al., Zygote 2005; 13:317-23.
Zhang et al., *Cell Res* 16:841-850, 2006.
Van Blerkom et al., *Hum Reprod* 10:415-424, 1995.
Folstad et al., Biotechnol. Prog. 2002 18(1):1-5.
Cohen et al., Mol Hum Reprod 1998; 4:269-80.
Barritt et al., Hum Reprod 2001; 16:513-6.
Muggleton-Harris et al., Nature 1982; 299:460-2.
Sutovsky et al., *Biol Reprod* 63:5820590, 2000.
CBER 2002 Meeting Documents, Biological Response Modifiers Advisory Committee minutes from May 9, 2002 (publically available from the FDA at http://www.fda.gov/BiologicsBloodVaccines/SafetyAvailability/ucm105852.htm).
Tarin et al., *Biol Reprod* 2001 65:141-150.
Sinclair Mech Ageing Dev 2005 126(9):987-1002.
Tarin et al., Hum Reprod 1995 10:1563-1565.
Yang et al., *Exp Gerontol* 2006 41: 718-726.
Van Blerkom et al., (*Human Reproduction* 13(10): 2857-2868, 1998).
Sugrue et al (Biol Signals Recept, 10(3-4): 176-88, (2001).
Short et al., PNAS USA, Apr. 12, 2005 102(15): 5618-5623.
Lu et al., Anal. Chem., Oct. 1, 2004 76(19): 5705-5712.
Raitz et al.: "Somatic cell cloning in polyester stacks", Proc. Natl. Acad. Sci. U.S.A. 1982; 17(10): 3223-7.
Esko:"Replica Plating of Animal Cells", Methods Cell Biology, 1989, 32:387-422.
Liu et al.: Global amplification polymerase chain reaction reveals novel transitional stages during osteoprogenitor differentiation, J. Cell Sci., 2003, 116(Pt. 9): 1787-96.
Sponsors/Researchers—Human Cells Used ion Therapy involving the Transfer of Genetic Material by Means Other Than the Union of Gamete Nuclei the FDA at htttp://www.fda.gov/BiologcsBloodVaccines/SafetyAvailability/ucm105852.htm (2001).
U.S. Appl. No. 13/447,075, filed Apr. 13, 2012, Tilly et al, Not Yet Published.
U.S. Appl. No. 13/447,083, filed Apr. 13, 2012, Tilly et al, Not Yet Published.
ISR issued in PCT/US2012/033643 (WO-2012/142500), Oct. 10, 2012, Tilly et al.
Written Opinion issued in PCT/US2012/033643 (WO-2012/142500), Oct. 10, 2012, Tilly et al.
ISR issued in PCT/US2012/033672, Oct. 16, 2012, Tilly et al.
Written Opinion issued in PCT/US2012/033672, Oct. 16, 2012, Tilly et al.
Zuckerman, Recent Prog Horm Res 1951; 6:63-108.
Zou et al., Nat Cell Biol 2009: 11:631-636.
Wang et al., Cell Cycle 2010; 9:339-349.
Niikura et al., Aging 2010; 2:999-1003.
Tilly et al., Biol Reprod 2009; 80:2-12.
Tilly et al., Mol Hum Reprod 2009; 15:393-398.
Niikura et al., Aging 2009; 1:971-978.
Massasa et al., Aging 2010; 2:1-2.
Matthews NCHS Data Brief 21:1-8, 2009.
Yang et al., ScienceDirect, Experimental Gerontology 41 (2006) 718-726.
Hunt et al., *Trends Genet* 24:86-93, 2008.
Tarin et al., *Mol Reprod Dev* 61:385-397, 2002.
Bentov et al., Fertil Steril 2010; 93(1):272-5. Epub Sep. 2009.
Harvey et al., Curr Top Dev Biol 2007; 77:229-49.
Acton et al., Biol Reprod 2007; 77: 569-76.
CBER 2002 Meeting Documents, Biological Response Modifiers Advisory Committee minutes from May 9, 2002 (publically available from the FDA at http://www.fda.gov/BiologicsBloodVaccines/SafetyAvailability/ucm105852.htm) Letter to.
Sponsors / Researchers—Human Cells Used in Therapy Involving the Transfer of Genetic Material by Means Other Than the Union of Gamete Nuclei (publically available from the FDA at http://www.fda.gov/BiologicsBloodVaccines/SafetyAvailability/ucm105852.htm), (2012).
Ramalho-Santos et al., *Hum Reprod Update*. 2009 (5):55 3-72.
Pachiarotti et al., *Differentiation* 2010 79:159-170.
Pan et al., *Dev Biol* 2008 316:397-407.
Duncan et al., *Biol Reprod* 2009 81:768-776.
Sinclair Mech Ageing Dev 2005 26:987.
Selesniemi et al. *Aging Cell* 7:622-629, 2008.
Yang et al., Cell 2008.
Hafner et al. *Aging* 2010 2:1-10Yang et al., *Exp Gerontol* 2006 41: 718-726.
Wang N et al., Inhibition of histone deacetylase activity amplifies retinoic acid-mediated induction of Stra8 expression and oogenesis in ovaries of adult female mice. Proceedings of the 41st Annual Meeting of the Society for the Study of Reproduction, Kailua-Kona, Big Island, HI (2008); p. 132 (Abstract 291).

FIG. 2A FIG. 2B
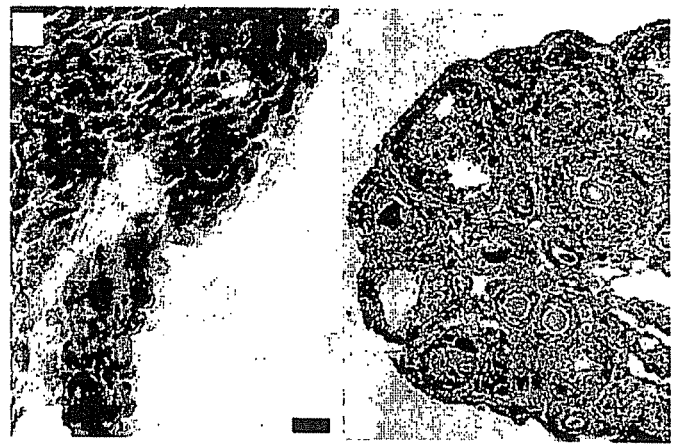
FIG. 2C FIG. 2D FIG. 2E
FIG. 2F FIG. 2G FIG. 2H
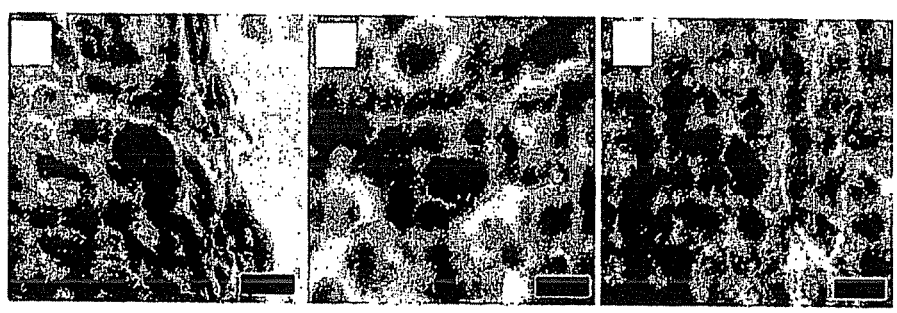

FIG. 4A  FIG. 4B  FIG. 4C
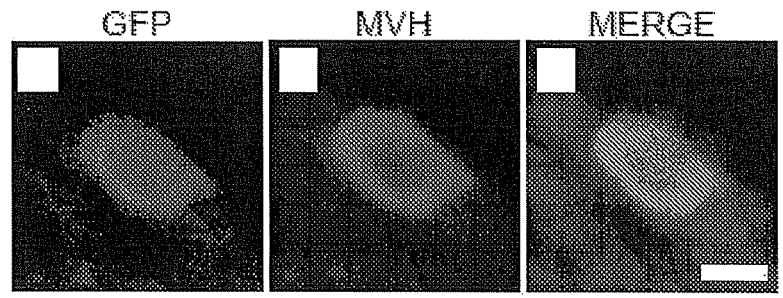
FIG. 4D  FIG. 4E  FIG. 4F
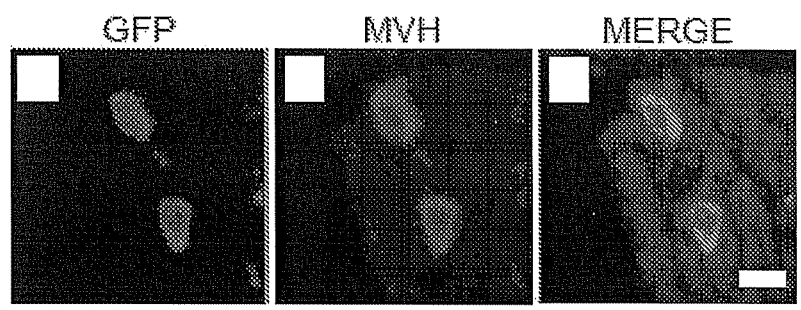
FIG. 4G  FIG. 4H  FIG. 4I
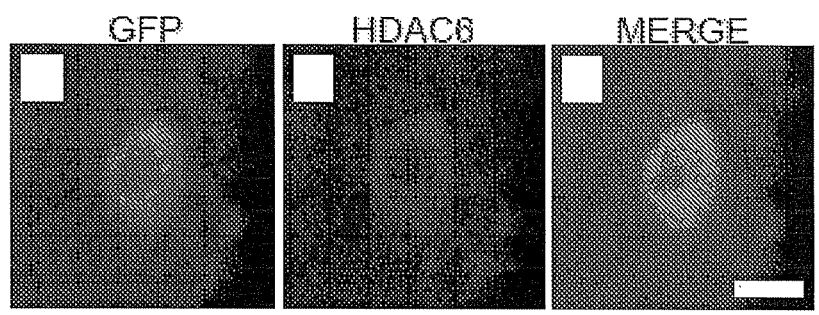

```
SEQUENCE LISTING

<160> NUMBER OF SEQ ID NOS: 2

<210> SEQ ID NO 1
<211> LENGTH: 27
<212> TYPE: DNA
<213> ORGANISM: Artificial Sequence
<220> FEATURE:
<223> OTHER INFORMATION: Primer

<400> SEQUENCE: 1
cacctcagag ggttttccaa gcgaggg                                      27

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
cctccttctg aacgggcctg a                                            21
```

METHODS OF TREATING FEMALE SUBJECTS IN NEED OF IN VITRO FERTILIZATION

RELATED APPLICATIONS/PATENTS & INCORPORATION BY REFERENCE

This application is a continuation of U.S. application Ser. No. 11/131,152, filed May 17, 2005, abandoned, which claims priority to U.S. provisional application Ser. No. 60/572,222, filed on May 17, 2004, provisional application Ser. No. 60/574,187, filed on May 24, 2004, and U.S. provisional application Ser. No. 60/586,641, filed on Jul. 9, 2004, the contents each of which are incorporated herein by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

STATEMENT OF GOVERNMENT INTEREST

The United States government has certain rights in this invention by virtue of grant numbers R01-AG12279 and R01-AG24999 from the National Institute on Aging and R01-ES08430 from the National Institute of Environmental Health Sciences of the National Institutes of Health.

SEQUENCE LISTING

This application contains a Sequence Listing that has been submitted electronically in ASCII text format and is hereby incorporated by reference in its entirety. Said ASCII text format, created on May 15, 2015, is named 051588.00010_SL.txt and is 772 bytes in size.

BACKGROUND OF THE INVENTION

A basic doctrine of reproductive biology, which states that mammalian females lose the capacity for germ-cell renewal during fetal life, has only recently been successfully challenged by Johnson et al., (2004) Nature 428: 145. Johnson et al. are the first to conclusively demonstrate that juvenile and adult mouse ovaries possess mitotically active germ cells that, based on rates of oocyte degeneration and clearance, sustain oocyte and follicle production in the postnatal mammalian ovary.

It has been recently determined that the precursors of germ cells are not confined exclusively to the ovaries. Germ cell marker genes have now been identified in cells derived from bone marrow. In addition, transplantation of bone marrow to a conditioned host allowed for bone marrow cell development into new oocytes within the ovary.

Umbilical cord blood from newborn infants is a known reservoir of stem cells that may contribute to a variety of somatic cell lineages, including hematopoietic precursors (for reviews see Korbling and Anderlini 2001 *Blood* 98: 2900-2908; Ho and Punzel, 2003 *J Leukoc Biol* 73: 547-555; Sanchez-Ramos 2002 *J Neurosci Res* 69: 880-893; Lee 2004 *Blood* 103:1669-75). Cord blood samples are easily and safely collected and may be stored for future therapeutic use (Rogers and Casper 2004 *Sexuality, Reproduction & Menopause* 2: 64-70); further, their availability to individual patients offers a potential source of perfectly-matched donor cells. It was heretofore unknown whether peripheral blood, such as cord blood also contained germ cell precursors.

SUMMARY OF THE INVENTION

Methods of the invention relate to the use of peripheral blood derived germline stem cells and their progenitor cells to, among other things, replenish or expand germ cell reserves of the testes and ovary, to enhance or restore fertility, and in females, to ameliorate symptoms and consequences of menopause.

In one aspect, the present invention provides compositions comprising peripheral blood derived female germline stem cells.

In one embodiment, the present invention provides compositions comprising peripheral blood derived female germline stem cells, wherein the cells are mitotically competent and express Vasa, Dazl, and Stella. Consistent with their mitotically competent phenotype, peripheral blood derived female germline stem cells of the invention do not express growth/differentiation factor-9 ("GDF-9"), zona pellucida proteins (e.g., zona pellucida protein-3, "ZP3"), histone deacetylase-6 ("HDAC6") and synaptonemal complex protein-3 ("SCP3").

Upon transplantation into a host, peripheral blood derived female germline stem cells of the invention can produce oocytes after a duration of at least 1 week, more preferably 1 to about 2 weeks, about 2 to about 3 weeks, about 3 to about 4 weeks or more than about 5 weeks post transplantation.

In another aspect, the present invention provides compositions comprising progenitor cells derived from peripheral blood derived female germline stem cells. In one embodiment, the present invention provides compositions comprising peripheral blood derived female germline stem cell progenitors, wherein the cells express Vasa, Dazl and Stella, and wherein the cells do not express GDF-9, zona pellucida proteins, HDAC6 and SCP3. Upon transplantation into a host, peripheral blood derived female germline stem cell progenitors of the invention can produce oocytes after a duration of less than 1 week, preferably about 24 to about 48 hours post transplantation.

In one embodiment, the present invention provides an isolated peripheral blood cell, wherein the cell is mitotically competent and expresses Vasa, Dazl and Stella. Preferably, the cell is a peripheral blood derived female germline stem cell, or its progenitor cell, having an XX karyotype. Preferably, the peripheral blood derived female germline stem cells, or their progenitor cells, are non-embryonic, mammalian, and even more preferably, human.

In another embodiment, the present invention provides purified populations of peripheral blood derived female germline stem cells and/or their progenitor cells. In specific embodiments, the purified population of cells is about 50 to about 55%, about 55 to about 60%, about 65 to about 70%, about 70 to about 75%, about 75 to about 80%, about 80 to about 85%, about 85 to about 90%, about 90 to about 95% or about 95 to about 100% of the cells in the composition.

In yet another embodiment, the present invention provides pharmaceutical compositions comprising peripheral blood derived female germline stem cells, and/or their progenitor cells, and a pharmaceutically acceptable carrier. The pharmaceutical compositions can comprise purified populations of peripheral blood derived female germline stem cells and/or their progenitor cells.

Compositions comprising peripheral blood derived germline stem cells of the invention can be provided by direct administration to ovarian tissue, or indirect administration, for example, to the circulatory system of a subject (e.g., to the extra-ovarian circulation).

In yet another aspect, the invention provides methods for manipulating peripheral blood derived germline stem cells, or their progenitor cells, in vivo, ex vivo or in vitro as described herein below.

In one embodiment, the invention provides a method for expanding peripheral blood derived female germline stem cells, or their progenitor cells, in vivo, ex vivo or in vitro, comprising contacting peripheral blood derived female germline stem cells, or their progenitor cells, with an agent that increases the amount of peripheral blood derived female germline stem cells, or their progenitor cells, by promoting proliferation or survival thereof, thereby expanding the peripheral blood derived female germline stem cells, or their progenitor cells. Such agents may promote mobilization of peripheral blood derived stem cells or of progenitor cells derived from peripheral blood derived stem cells from within the peripheral blood into the peripheral blood (e.g., GCSF, GMCSF). In a preferred embodiment, the agent includes, but is not limited to, a hormone or growth factor (e.g., insulin-like growth factor ("IGF"), transforming growth factor ("TGF"), bone morphogenic protein ("BMP"), Wnt protein, or fibroblast growth factor ("FGF")), a cell-signaling molecule (e.g., sphingosine-1-phosphate ("SIP"), or retinoic acid ("RA")), or a pharmacological or pharmaceutical compound (e.g., an inhibitor of glycogen synthase kinase-3 ("GSK-3"), an inhibitor of apoptosis such as a Bax inhibitor or a caspase inhibitor, an inhibitor of nitric oxide production, or an inhibitor of MAC activity).

In another embodiment, the invention provides a method for identifying an agent that promotes proliferation or survival of a peripheral blood derived female germline stem cell, or its progenitor cell, comprising contacting the peripheral blood derived female germline stem cells, or their progenitor cells, with a test agent; and detecting an increase in the number of peripheral blood derived female germline stem cells, or their progenitor cells, thereby identifying an agent that promotes proliferation or survival of a peripheral blood derived female germline stem cell, or its progenitor cell.

In yet another embodiment, the invention provides a method for using the female germline stem cells, or their progenitor cells, to characterize pharmacogenetic cellular responses to biologic or pharmacologic agents, comprising isolating peripheral blood derived female germline stem cells, or their progenitor cells, from a population of subjects, expanding said cells in culture to establish a plurality of cell cultures, optionally differentiating said cells into a desired lineage, contacting the cell cultures with one or more biologic or pharmacologic agents, identifying one or more cellular responses to the one or more biologic or pharmacologic agents, and comparing the cellular responses of the cell cultures from different subjects.

In yet another embodiment, the invention provides a method for oocyte production, comprising culturing a peripheral blood derived female germline stem cell, or its progenitor cell, in the presence of an agent that differentiates a peripheral blood derived female germline stem cell, or its progenitor cell, into an oocyte, thereby producing an oocyte. In a preferred embodiment, the agent includes, but is not limited to, a hormone or growth factor (e.g., a TGF, BMP or Wnt family protein, kit-ligand ("SCF") or leukemia inhibitory factor ("LIF")), a signaling molecule (e.g., meiosis-activating sterol, "FF-MAS"), or a pharmacologic or pharmaceutical agent (e.g., a modulator of Id protein function or Snail/Slug transcription factor function).

In yet another embodiment, the invention provides a method for in vitro fertilization of a female subject, said method comprising the steps of:
 a) producing an oocyte by culturing a peripheral blood derived female germline stem cell, or its progenitor, in the presence of an oocyte differentiation agent;
 b) fertilizing the oocyte in vitro to form a zygote; and
 c) implanting the zygote into the uterus of a female subject.

In yet another embodiment, the invention provides a method for in vitro fertilization of a female subject, said method comprising the steps of
 a) producing an oocyte by contacting a peripheral blood derived female germline stem cell, or its progenitor cell, with an agent that differentiates said cell(s) into an oocyte;
 b) fertilizing the oocyte in vitro to form a zygote; and
 c) implanting the zygote into the uterus of a female subject.

In yet another embodiment, the invention provides a method for identifying an agent that induces differentiation of a peripheral blood derived female germline stem cell, or its progenitor cell, into an oocyte comprising contacting peripheral blood derived female germline stem cells, or their progenitor cells, with a test agent; and detecting an increase in the number of oocytes, thereby identifying an agent that induces differentiation of a peripheral blood derived female germline stem cell, or its progenitor.

In yet another embodiment, the present invention provides a method for oocyte production, comprising providing a peripheral blood derived female germline stem cell, or its progenitor cell, to a tissue, preferably the ovary, wherein the cell engrafts into the tissue and differentiates into an oocyte, thereby producing an oocyte.

In yet another embodiment, the present invention provides a method for inducing folliculogenesis, comprising providing a peripheral blood derived female germline stem cell, or its progenitor cell, to a tissue, preferably the ovary, wherein the cell engrafts into the tissue and differentiates into an oocyte within a follicle, thereby inducing folliculogenesis.

In yet another embodiment, the present invention provides a method for treating infertility in a female subject in need thereof comprising administering a therapeutically effective amount of a composition comprising peripheral blood derived female germline stem cells, or their progenitor cells, to the subject, wherein the cells engraft into a tissue, preferably ovarian tissue, and differentiate into oocytes, thereby treating infertility. Except where expressly stated herein, the female subject in need of fertility treatment is not a subject who has undergone prior chemotherapy or radiotherapy.

In yet another embodiment, the present invention provides a method for restoring fertility to a female subject having undergone chemotherapy or radiotherapy (or both treatments) and who desires restored fertility, comprising administering a therapeutically effective amount of peripheral blood derived female germline stem cells, or their progenitor cells, to the subject, wherein the cells engraft into a tissue, preferably ovarian tissue, and differentiate into oocytes, thereby restoring fertility in the subject. Preferably, the peripheral blood derived female germline stem cells comprise a purified sub-population of cells obtained from the peripheral blood. Chemotherapeutic drugs include, but are not limited to, busulfan, cyclophosphamide, 5-FU, vinblastine, actinomycin D, etoposide, cisplatin, methotrexate, doxorubicin, among others. Radiotherapy includes, but is not limited to, ionizing radiation, ultraviolet radiation, X-rays, and the like.

In yet another embodiment, the present invention provides a method for protecting fertility in a female subject undergoing or expected to undergo chemotherapy or radiotherapy (or both treatments), comprising providing an agent that protects against reproductive injury prior to or concurrently with chemotherapy or radiotherapy (or both treatments) and providing a peripheral blood derived female germline stem cell, or its progenitor cell, to the subject, wherein the cell engrafts into a tissue, preferably ovarian tissue, and differentiates into an oocyte, thereby protecting fertility in the subject. The protective agent can be S1P, a Bax antagonist, or any agent that increases SDF-1 activity.

In yet another embodiment, the present invention provides a method for repairing damaged ovarian tissue, comprising providing a therapeutically effective amount of a composition comprising peripheral blood derived female germline stem cells, or their progenitor cells, to the tissue, wherein the cells engraft into the tissue and differentiate into oocytes, thereby repairing the damaged tissue. Damage can be caused, for example, by exposure to cytotoxic factors, hormone deprivation, growth factor deprivation, cytokine deprivation, cell receptor antibodies, and the like. Except where expressly stated herein, the damage is not caused by prior chemotherapy or radiotherapy. Damage can also be caused be diseases that affect ovarian function, including, but not limited to cancer, polycystic ovary disease, genetic disorders, immune disorders, metabolic disorders, and the like.

In yet another embodiment, the present invention provides a method for restoring ovarian function in a female subject having undergone chemotherapy or radiotherapy (or both treatments) and who desires restored ovarian function, comprising administering a therapeutically effective amount of peripheral blood derived female germline stem cells, or their progenitor cells, to an ovary of the subject, wherein the cells engraft into the ovary and differentiate into oocytes within the ovary, thereby restoring ovarian function in the subject.

In yet another embodiment, the present invention provides a method for restoring ovarian function in a menopausal female subject, comprising administering a therapeutically effective amount of a composition comprising peripheral blood derived female germline stem cells, or their progenitor cells, to the subject, wherein the cells engraft into the ovary and differentiate into oocytes, thereby restoring ovarian function. The menopausal female subject can be in a stage of either peri- or post-menopause, with said menopause caused by either normal (e.g., aging) or pathological (e.g., surgery, disease, ovarian damage) processes.

Restoration of ovarian function can relieve adverse symptoms and complications associated with menopausal disorders, including, but not limited to, somatic disorders such as osteoporosis, cardiovascular disease, somatic sexual dysfunction, hot flashes, vaginal drying, sleep disorders, depression, irritability, loss of libido, hormone imbalances, and the like, as well as cognitive disorders, such as loss of memory; emotional disorders, depression, and the like.

In yet another embodiment, the present invention provides a method for detecting or diagnosing premature ovarian failure in a subject, comprising determining the number of female germline stem cells, or their progenitors, present in a sample of peripheral blood obtained from the subject, wherein the number of female germline stem cells, or their progenitors, in the sample is substantially less than the number of female germline stem cells, or their progenitors, in a sample obtained from a healthy subject, thereby detecting or diagnosing premature ovarian failure in the subject.

Methods of the present invention can be used in the production of other reproductive cell types. Accordingly, in yet another aspect, the present invention provides compositions comprising peripheral blood derived male germline stem cells, wherein the peripheral blood derived male germline stem cells are mitotically competent and express Vasa and Dazl. Peripheral blood derived male germline stem cells of the invention have an XY karyotype, whereas peripheral blood derived female germline stem cells of the invention have an XX karyotype. Preferably, the peripheral blood derived male germline stem cells are non-embryonic, mammalian, and even more preferably, human.

In one embodiment, the invention provides an isolated peripheral blood cell that is mitotically competent, has an XY kayrotype and expresses Vasa and Dazl.

In another embodiment, the present invention provides a method for restoring or enhancing spermatogenesis, comprising providing a peripheral blood derived male germline stem cell, or its progenitor cell, to the testes of a male subject, wherein the cell engrafts into the seminiferous epithelium and differentiates into a sperm cell, thereby restoring or enhancing spermatogenesis.

In yet another embodiment, the present invention provides a method for restoring fertility to a male subject having undergone chemotherapy or radiotherapy (or both) and who desires restored fertility, comprising administering a therapeutically effective amount of peripheral blood derived male germline stem cells, or their progenitor cells, to the subject, wherein the cells engraft into the seminiferous epithelium and differentiate into sperm cells, thereby restoring fertility.

In yet another embodiment, the invention provides a method for reducing the amount of peripheral blood derived germline stem cells, or their progenitor cells, in vivo, ex vivo or in vitro, comprising contacting peripheral blood derived germline stem cells, or their progenitor cells, with an agent that reduces cell proliferation, thereby reducing the amount of peripheral blood derived germline stem cells, or their progenitor cells. In a preferred embodiment, the agent includes, but is not limited to, a hormone or growth factor (e.g., TGF-β), a peptide antagonist of mitogenic hormones or growth factors (e.g., the BMP antagonists, Protein Related to DAN and Cerberus ("PRDC") and Gremlin), or a pharmacological or pharmaceutical compound (e.g., a cell cycle inhibitor, or an inhibitor of growth factor signaling).

In yet another embodiment, the invention provides a method for reducing the amount of peripheral blood derived germline stem cells, or their progenitor cells, in vivo, ex vivo or in vitro, comprising contacting peripheral blood derived germline stem cells, or their progenitor cells, with an agent that inhibits cell survival or promotes cell death, thereby reducing the amount of peripheral blood derived germline stem cells, or their progenitor cells. In a preferred embodiment, the agent the that inhibits cell survival includes, but is not limited to, a hormone, growth factor or cytokine (e.g., a pro-apoptotic tumor necrosis factor ("TNF") super family member such as TNF-α, Fas-ligand ("FasL") and TRAIL), an antagonist of pro-survival Bcl-2 family member function, a signaling molecule (e.g., a ceramide), or a pharmacological or pharmaceutical compound (e.g., an inhibitor of growth factor signaling). In a preferred embodiment, the agent the that promotes cell death includes, but is not limited to, a pro-apoptotic tumor necrosis factor superfamily member (e.g., TNF-α, FasL and TRAIL), agonist of pro-apoptotic Bcl-2 family member function and ceramide.

In yet another embodiment, the invention provides a method for identifying an agent that reduces proliferation or survival, or promotes cell death, of a peripheral blood derived germline stem cell, or its progenitor cell, comprising contacting peripheral blood derived germline stem cells, or their progenitor cells, with a test agent; and detecting a decrease in the number of peripheral blood derived germline stem cells, or their progenitor cells, thereby identifying an agent that reduces proliferation or survival, or promotes cell death, of a female germline stem cell, or its progenitor cell.

In yet another embodiment, the present invention provides a method for contraception in a male or female subject comprising contacting peripheral blood derived germline stem cells, or their progenitor cells, of the subject with an agent that decreases the proliferation, function or survival of peripheral blood derived germline stem cells, or their progenitor cells, or the ability of said cells to produce new oocytes or sperm cells or other somatic cell types required for fertility, thereby providing contraception to the subject.

In yet another aspect, the present invention provides kits for use in employing various agents of the invention.

In one embodiment, the present invention provides a kit for expanding a peripheral blood derived female germline stem cell, or its progenitor cell, in vivo, ex vivo or in vitro, comprising an agent that promotes cell proliferation or survival of the peripheral blood derived female germline stem cell, or its progenitor cell, and instructions for using the agent to promote cell proliferation or survival of the peripheral blood derived female germline stem cell, or its progenitor, thereby expanding a female germline stem cell, or its progenitor cell in accordance with the methods of the invention.

In another embodiment, the present invention provides a kit for oocyte production, comprising an agent that differentiates a peripheral blood derived female germline stem cell, or its progenitor cell, into an oocyte and instructions for using the agent to differentiate a peripheral blood derived female germline stem cell, or its progenitor cell, into an oocyte in accordance with the methods of the invention.

In yet another embodiment, the present invention provides a kit for oocyte production, comprising an agent that increases the amount of peripheral blood derived female germline stem cells, or their progenitor cells, by promoting proliferation or survival thereof, and instructions for using the agent to increase the amount of peripheral blood derived female germline stem cells or their progenitor cells, thereby producing oocytes in accordance with the methods of the invention.

In yet another embodiment, the present invention provides a kit for oocyte production comprising an agent that differentiates peripheral blood derived female germline stem cells, or their progenitor cells, into oocytes and instructions for using the agent to differentiate the peripheral blood derived female germline stem cells, or their progenitor cells, into oocytes, thereby producing oocytes in accordance with the methods of the invention.

In yet another embodiment, the present invention provides a kit for treating infertility in a female subject in need thereof comprising an agent that increases the amount of peripheral blood derived female germline stem cells, or their progenitor cells, by promoting proliferation or survival thereof and instructions for using the agent to increase the amount of peripheral blood derived female germline stem cells or their progenitor cells, thereby treating infertility in the subject in accordance with the methods of the invention.

In yet another embodiment, the present invention provides a kit for treating infertility in a female subject in need thereof comprising an agent that differentiates peripheral blood derived female germline stem cells, or their progenitor cells, into oocytes, and instructions for using the agent to differentiate peripheral blood derived female germline stem cells, or their progenitor cells, into oocytes, thereby treating infertility in the subject in accordance with the methods of the invention.

In yet another embodiment, the present invention provides a kit for protecting fertility in a female subject undergoing or expected to undergo chemotherapy or radiotherapy (or both treatments), comprising an agent that that protects peripheral blood derived female germline stem cells, or their progenitor cells, against reproductive injury and instructions for using the agent to protect peripheral blood derived female germline stem cells, or their progenitor cells, against reproductive injury thereby protecting fertility in the female subject in accordance with the methods of the invention.

In yet another embodiment, the present invention provides a kit for restoring ovarian function in a post-menopausal female subject comprising an agent that increases the amount of peripheral blood derived female germline stem cells, or their progenitor cells, by promoting proliferation or survival thereof and instructions for using the agent to increase the amount of peripheral blood derived female germline stem cells or their progenitor cells, thereby restoring ovarian function in the subject in accordance with the methods of the invention.

In yet another embodiment, the present invention provides a kit for restoring ovarian function in a post-menopausal female subject comprising an agent that differentiates peripheral blood derived female germline stem cells, or their progenitor cells, into oocytes, and instructions for using the agent to differentiate peripheral blood derived female germline stem cells, or their progenitor cells, into oocytes, thereby restoring ovarian function in the subject in accordance with the methods of the invention.

In another embodiment, the present invention provides a kit for reducing the amount of peripheral blood derived germline stem cells, or their progenitor cells, in vivo, ex vivo or in vitro, comprising an agent that inhibits cell survival or promotes cell death and instructions for using the agent to inhibit cell survival or promote cell death of the peripheral blood derived germline stem cells, or their progenitor cells, thereby the reducing the amount of peripheral blood derived germline stem cells, or their progenitor cells, in accordance with the methods of the invention.

In yet another embodiment, the present invention provides a kit for contraception in a male of female subject comprising an agent that decreases the proliferation, function or survival of peripheral blood derived germline stem cells, or their progenitor cells, or the ability of said cells to produce new oocytes or other somatic cell types required for fertility and instructions for using the agent to decrease the proliferation, function or survival of peripheral blood derived germline stem cells, or their progenitor cells, or the ability of said cells to produce new oocytes or sperm cells or other somatic cell types required for fertility, thereby providing contraception to the subject in accordance with the methods of the invention.

BRIEF DESCRIPTION OF THE DRAWINGS

FIG. 1 depicts results indicating that peripheral blood contains oocyte-producing germ cells.

FIG. 2 depicts further results indicating that peripheral blood contains oocyte-producing germ cells. Follicles containing GFP-positive (brown) oocytes in ovaries of adult Oct4-GFP transgenic mice (A, multiple primordial oocytes are highlighted). Scale bar=10 mm. Oocytes (arrowhead or boxed) in a wild-type ovary prior to PBCT using Oct4-GFP (TgOG2) females as donors, showing a lack of GFP signal (inset, primordial oocyte) (C). Primordial follicles containing GFP-positive oocytes in ovaries of wild-type female mice 28-30 hr after PBCT, using adult TgOG2 transgenic females as peripheral blood cell donors (see also FIG. 8) (D-F). Scale bars=10 mm. GFP-positive primordial oocytes in ovaries of Atm-deficient females 30 h after PBCT using adult TgOG2 transgenic females as donors (G-H). Scale bars=10 mm.

DETAILED DESCRIPTION OF THE INVENTION

Definitions

Figures 1A, 1B, 1C:
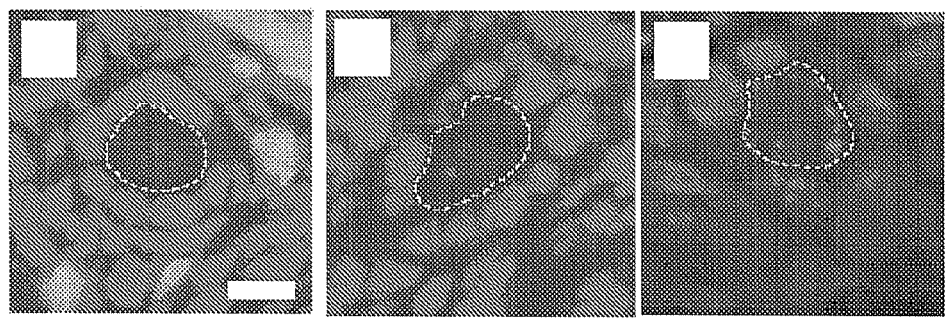
FIG. 1A shows a primordial-early primary follicle containing a GFP-positive oocyte (green, encircled within white dashed line; nuclei visualized by propidium iodide in red) in an adult GFP-transgenic mouse (scale bar=10 mm).
FIG. 1B shows an early primary oocyte in a wild-type ovary prior to PBCT, showing a lack of GFP signal (compare with a).
FIGS. 1C-E, show examples of primordial and early primary follicles containing GFP-positive oocytes (compare with a) in ovaries of wild-type mice 24 hours after PBCT using peripheral blood harvested from adult GFP-transgenic females.

"Peripheral blood derived germline stem cells" are any multipotent cells obtained from peripheral blood that include a population of male or female germline stem cells.

"Expansion" refers to the propagation of a cell or cells without terminal differentiation. "Isolation phenotype" refers to the structural and functional characteristics of the peripheral blood derived germline stem cells upon isolation. "Expansion phenotype" refers to the structural and functional characteristics of the peripheral blood derived germline stem cells during expansion. The expansion phenotype can be identical to the isolation phenotype, or alternatively, the expansion phenotype can be more differentiated than the isolation phenotype.

"Differentiation" refers to the developmental process of lineage commitment. A "lineage" refers to a pathway of cellular development, in which precursor or "progenitor" cells undergo progressive physiological changes to become a specified cell type having a characteristic function (e.g., nerve cell, muscle cell or endothelial cell). Differentiation occurs in stages, whereby cells gradually become more specified until they reach full maturity, which is also referred to as "terminal differentiation." A "terminally differentiated cell" is a cell that has committed to a specific lineage, and has reached the end stage of differentiation (i.e., a cell that has fully matured). Oocytes are an example of a terminally differentiated cell type.

The term "isolated" as used herein refers to a peripheral blood derived germline stem cell or its progenitor cell, in a non-naturally occurring state (e.g., isolated from the body or a biological sample, such as peripheral blood, from the body).

"Progenitor cells" as used herein are germ lineage cells that are 1) derived from germline stem cells of the invention as the progeny thereof which contain a set of common marker genes; 2) are in an early stage of differentiation; and 3) retain mitotic capacity.

"Progeny" as used herein are all cells derived from peripheral blood derived germline stem cells of the invention, including progenitor cells, differentiated cells, and terminally differentiated cells.

"Derived from" as used herein refers to the process of obtaining a daughter cell.

"Engraft" refers to the process of cellular contact and incorporation into an existing tissue of interest (e.g., ovary) in vivo.

"Agents" refer to cellular (e.g., biologic) and pharmaceutical factors, preferably growth factors, cytokines, hormones or small molecules, or to genetically-encoded products that modulate cell function (e.g., induce lineage commitment, increase expansion, inhibit or promote cell growth and survival). For example, "expansion agents" are agents that increase proliferation and/or survival of peripheral blood derived germline stem cells. "Differentiation agents" are agents that induce peripheral blood derived germline stem cells to differentiate into committed cell lineages, such as oocytes or sperm cells.

A "follicle" refers to an ovarian structure consisting of a single oocyte surrounded by somatic (granulosa without or with theca-interstitial) cells. Somatic cells of the gonad enclose individual oocytes to form follicles. Each fully formed follicle is enveloped in a complete basement membrane. Although some of these newly formed follicles start to grow almost immediately, most of them remain in the resting stage until they either degenerate or some signal(s) activate(s) them to enter the growth phase. For reviews on ovarian structure, function and physiology, see Gougeon, A., (1996) Endocr Rev. 17:121-55; Anderson, L. D., and Hirshfield, A. N. (1992) Md Med J. 41: 614-20; and Hirshfield, A. N. (1991) hit Rev Cytol. 124: 43-101.

A "sperm cell" refers to a male germ cell, in either a pre-meiotic (i.e., mitotically competent) or post-meiotic state of development, including a fully mature spermatozoan. "Spermatogenesis" is the developmental process by which a sperm cell is formed.

"Mitotically competent" refers to a cell that is capable of mitosis, the process by which a cell divides and produces two daughter cells from a single parent cell.

A "non-embryonic" cell refers to a cell that is obtained from a post-natal source (e.g., infant, child or adult tissue).

A "subject" is a vertebrate, preferably a mammal, more preferably a primate and still more preferably a human. Mammals include, but are not limited to, primates, humans, farm animals, sport animals, and pets.

The term "obtaining" as in "obtaining the agent" is intended to include purchasing, synthesizing or otherwise acquiring the agent (or indicated substance or material).

The terms "comprises", "comprising", and are intended to have the broad meaning ascribed to them in U.S. Patent Law and can mean "includes", "including" and the like.

EMBODIMENTS OF THE INVENTION

I. Peripheral Blood Derived Germline Stem Cells

Methods of the invention relate to the use of peripheral blood derived germline stem cells, or progenitors of peripheral blood derived germline stem cells, to restore or increase germ cell production. Methods of the invention can be used to, among other things, enhance or restore fertility, and in females, to ameliorate symptoms and consequences of menopause.

Without wanting to be bound by theory, it is understood that one or more mechanisms can be involved with the ability of peripheral blood derived germline stem cells to repopulate the germ cell population. Female germline stem cells have been detected in the peripheral blood, which may therefore serve as a reservoir for stem cells having the capacity to repopulate and/or expand the germ cell supply of reproductive organs. Male germline stem cells can also exist in the peripheral blood of male subjects. Other sub-populations of cells in the peripheral blood, such as hematopoietic stem cells, may likewise have the ability to repopulate and/or expand the germ cell supply of reproductive organs, for example, through de-differentiation into a multipotent progenitor cell (see U.S. Pat. No. 6,090,625; Herzog, E. L., et al., (2004) Blood 102(10): 3483) which in turn migrates through peripheral blood to the reproductive tract, engrafts into an organ (e.g., ovary or testes) as a germline stem cell or a progenitor of a germline stem cell and differentiates into a germ cell.

As described herein, germline stem cells have been detected in the peripheral blood (including cord blood) of male and female subjects. Peripheral blood derived female germline stem cells express markers including Vasa, Dazl, and Stella. Peripheral blood derived female germline stem cells are mitotically competent (i.e., capable of mitosis) and accordingly, do not express GDF-9, zona pellucida proteins (e.g., ZP3), HDAC6 or SCP3.

The present invention also provides peripheral blood derived female germline stem cell progenitors. Peripheral blood derived female germline stem cell progenitors of the invention can circulate throughout the body and most preferably can be localized in bone marrow, peripheral blood and ovary. Progenitor cells of the invention express Vasa, Dazl, and Stella but do not express GDF-9, zona pellucida proteins (e.g., ZP3), HDAC6 or SCP3.

Peripheral blood derived female germline stem cells and their progenitor cells have functional distinctions. Upon transplantation into a host, peripheral blood derived female germline stem cells of the invention can produce oocytes after a duration of at least 1 week, more preferably 1 to about 2 weeks, about 2 to about 3 weeks, about 3 to about 4 weeks or more than about 5 weeks post transplantation. Peripheral blood derived female germline stem cell progenitors have the capacity to generate oocytes more rapidly than peripheral blood derived female germline stem cells. Upon transplantation into a host, peripheral blood derived female germline stem cell progenitors of the invention can produce oocytes after a duration of less than 1 week, preferably about 24 to about 48 hours post transplantation.

Stella is a gene expressed in peripheral blood derived female germline stem cells and their progenitor cells. Stella is a novel gene specifically expressed in primordial germ cells and their descendants, including oocytes (Bortvin et al. (2004) BMC Developmental Biology 4(2):1-5). Stella encodes a protein with a SAP-like domain and a splicing factor motif-like structure. Embryos deficient in Stella expression are compromised in preimplantation development and rarely reach the blastocyst stage. Thus, Stella is a maternal factor implicated in early embryogenesis.

Dazl is a gene expressed in peripheral blood derived female germline stem cells and their progenitor cells. The autosomal gene Dazl is a member of a family of genes that contain a consensus RNA binding domain and are expressed in germ cells. Loss of expression of an intact Dazl protein in mice is associated with failure of germ cells to complete meiotic prophase. Specifically, in female mice null for Dazl, loss of germ cells occurs during fetal life at a time coincident with progression of germ cells through meiotic prophase. In male mice null for Dazl, germ cells were unable to progress beyond the leptotene stage of meiotic prophase I. Thus, in the absence of Dazl, progression through meiotic prophase is interrupted (Saunders et al. (2003), Reproduction, 126:589-597).

Vasa is a gene expressed in peripheral blood derived female germline stem cells and their progenitor cells. Vasa is a component of the germplasm that encodes a DEAD-family ATP-dependent RNA helicase (Liang et al. (1994) Development, 120:1201-1211; Lasko et al. (1988) Nature, 335:611-167). The molecular function of Vasa is directed to binding target mRNAs involved in germ cell establishment (e.g., Oskar and Nanos), oogenesis, (e.g., Gruken), and translation onset (Gavis et al. (1996) Development, 110: 521-528). Vasa is required for pole cell formation and is exclusively restricted to the germ cell lineage throughout the development. Thus, Vasa is a molecular marker for the germ cell lineage in most animal species (Toshiaki et al. (2001) Cell Structure and Function 26:131-136). Because Vasa has been associated with inhibition of cell migration, expression of Vasa in progenitor cells of the invention may be differentially regulated, depending on the migratory state of the progenitor. For example, while in the bone marrow, the progenitor may express Vasa, and while migrating to the reproductive tract, the progenitor may down regulate expression.

Peripheral blood derived female germline stem cells and their progenitor cells do not express GDF-9, a gene expressed in cells that have already started to differentiate into oocytes. Growth/differentiation factor-9 (GDF-9) is a member of the transforming growth factor-β superfamily, expressed specifically in ovaries. GDF-9 mRNA can be found in neonatal and adult oocytes from the primary one-layer follicle stage until after ovulation (Dong, J. et al (1996) Nature 383: 531-5). Analysis of GDF-9 deficient mice reveals that only primordial and primary one-layer follicles can be formed, but a block beyond the primary one-layer follicle stage in follicular development occurs, resulting in complete infertility.

Peripheral blood derived female germline stem cells and their progenitor cells do not express ZP3, ZP1, ZP2, and ZP3, which are gene products that comprise the zona pellucida of the oocyte. Their expression is regulated by a basic helix-loop-helix (bHLH) transcription factor, FIGα. Mice null in FIGα do not express the Zp genes and do not form primordial follicles (Soyal, S. M., et al (2000) Development 127: 4645-4654). Individual knockouts of the ZP genes result in abnormal or absent zonae pellucidae and decreased fertility (Zp1; Rankin T, et al (1999) Development. 126: 3847-55) or sterility (Zp2, Rankin T L, et al. (2001) Development 128: 1119-26; ZP3, Rankin T et al (1996) Development 122: 2903-10). The ZP protein products are glycosylated, and subsequently secreted to form an extracellular matrix, which is important for in vivo fertilization and pre-implantation development. Expression of the ZP proteins is precisely regulated and restricted to a two-week growth phase of oogenesis. Zp mRNA transcripts are not expressed in resting oocytes, however once the oocytes begin to grow, all three Zp transcripts begin to accumulate.

Peripheral blood derived female germline stem cells and their progenitor cells do not express HDAC6. HDACs, or histone deacetylases are involved in ovarian follicle development. HDAC6 in particular can be detected in resting germinal vesicle-stage (primordial) oocytes (Verdel, A., et al. (2003) Zygote 11: 323-8; FIG. 16). HDAC6 is a class II histone deacetylase and has been implicated as a microtubule-associated deactylase (Hubbert, C. et al, (2002) Nature 417: 455-8). HDACs are the target of inhibitors including, but not limited to, trichostatin A and trapoxin, both of which are microbial metabolites that induce cell differentiation, cell cycle arrest, and reversal of the transformed cell morphology.

Peripheral blood derived female germline stem cells and their progenitor cells do not express SCP3, consistent with observations that they are pre-meiotic stem cells (i.e., diploid). The synaptonemal complex protein SCP3 is part of the lateral element of the synaptonemal complex, a meiosis-specific protein structure essential for synapsis of homologous chromosomes. The synaptonemal complex promotes pairing and segregation of homologous chromosomes, influences the number and relative distribution of crossovers, and converts crossovers into chiasmata. SCP3 is meiosis-specific and can form multi-stranded, cross-striated fibers, forming an ordered, fibrous core in the lateral element (Yuan, L. et al, (1998) J. Cell. Biol. 142: 331-339). The absence of SCP3 in mice can lead to female genii cell aneuploidy and embryo death, possibly due to a defect in structural integrity of meiotic chromosomes (Yuan, L. et al, (2002) Science 296: 1115-8).

Peripheral blood derived female germline stem cells and their progenitor cells can be isolated by standard means known in the art for the separation of stem cells from the blood(e.g., cell sorting). Preferably, the isolation protocol includes generation of a kit$^+$/lin$^-$ fraction that is depleted of hematopoietic cells. Additional selection means based on the unique profile of gene expression (e.g., Vasa, Dazl and Stella) can be employed to further purify populations of cells comprising peripheral blood derived female germline stem cells and their progenitor cells. Compositions comprising peripheral blood derived female germline stem cells and their progenitor cells can be isolated and subsequently purified to an extent where they become substantially free of the biological sample from which they were obtained (e.g. peripheral blood, including umbilical cord blood).

Peripheral blood derived female germline stem cell progenitors can be obtained from peripheral blood female germline stem cells by, for example, expansion in culture. Thus, the progenitor cells can be cells having an "expansion phenotype."

II. Administration

Compositions comprising peripheral blood derived germline stem cells or their progenitors can be provided directly to the reproductive organ of interest (e.g., ovary or testes). Alternatively, compositions comprising peripheral blood derived germline stem cells or their progenitors can be provided indirectly to the reproductive organ of interest, for example, by administration into the circulatory system (e.g., to extra-ovarian circulation). Following transplantation or implantation, the cells can engraft and differentiate into germ cells (e.g., oocytes or sperm cells). "Engraft" refers to the process of cellular contact and incorporation into an existing tissue of interest (e.g., ovary) in vivo. Expansion and differentiation agents can be provided prior to, during or after administration to increase production of germ cells in vivo.

Compositions of the invention include pharmaceutical compositions comprising peripheral blood derived germline stem cells or their progenitors and a pharmaceutically acceptable carrier. Administration can be autologous or heterologous. For example, peripheral blood derived germline stem cells, or progenitors derived from peripheral blood derived germline stem cells, can be obtained from one subject, and administered to the same subject or a different, compatible subject.

Peripheral blood derived germline stem cells of the invention or their progeny (e.g., in vivo, ex vivo or in vitro derived) can be administered via localized injection, including catheter administration, systemic injection, localized injection, intravenous injection, intrauterine injection or parenteral administration. When administering a therapeutic composition of the present invention (e.g., a pharmaceutical composition), it will generally be formulated in a unit dosage injectable form (solution, suspension, emulsion).

Compositions of the invention can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the cells utilized in practicing the present invention in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the peripheral blood derived germline stem cells or their progenitors.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled fowl).

A method to potentially increase cell survival when introducing the cells into a subject in need thereof is to incorporate peripheral blood derived germline stem cells or their progeny (e.g., in vivo, ex vivo or in vitro derived) of interest into a biopolymer or synthetic polymer. Depending on the subject's condition, the site of injection might prove inhospitable for cell seeding and growth because of scarring or other impediments. Examples of biopolymer include, but are not limited to, cells mixed with fibronectin, fibrin, fibrinogen, thrombin, collagen, and proteoglycans. This could be constructed with or without included expansion or differentiation factors. Additionally, these could be in suspension, but residence time at sites subjected to flow would be nominal. Another alternative is a three-dimensional gel with cells entrapped within the interstices of the cell biopolymer admixture. Again, expansion or differentiation factors could be included with the cells. These could be deployed by injection via various routes described herein.

Those skilled in the art will recognize that the components of the compositions should be selected to be chemically inert and will not affect the viability or efficacy of the peripheral blood derived germline stem cells or their progenitors as described in the present invention. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of peripheral blood derived germline stem cells of the invention is the quantity of cells necessary to achieve an optimal effect. In current human studies of autologous mononuclear peripheral blood cells, empirical doses ranging from 1 to $4 \times 10^7$ cells have been used with encouraging results. However, different scenarios may require optimization of the amount of cells injected into a tissue of interest. Thus, the quantity of cells to be administered will vary for the subject being treated. In a preferred embodiment, between $10^4$ to $10^8$, more preferably $10^5$ to $10^7$, and still more preferably, $3 \times 10^7$ stem cells of the invention can be administered to a human subject.

Less cells can be administered directly to the ovary or testes. Preferably, between $10^2$ to $10^6$, more preferably $10^3$ to $10^5$, and still more preferably, $10^4$ peripheral blood derived germline stem cells can be administered to a human subject. However, the precise determination of what would be considered an effective dose may be based on factors individual to each patient, including their size, age, sex, weight, and condition of the particular patient. As few as 100-1000 cells can be administered for certain desired applications among selected patients. Therefore, dosages can be readily ascertained by those skilled in the art from this disclosure and the knowledge in the art.

Peripheral blood derived germline stem cells of the invention can comprise a purified population of female germline stem cells. Those skilled in the art can readily determine the percentage of female germline stem cells in a population using various well-known methods, such as fluorescence activated cell sorting (FACS). Preferable ranges of purity in populations comprising female germline stem cells are about 50 to about 55%, about 55 to about 60%, and about 65 to about 70%. More preferably the purity is about 70 to about 75%, about 75 to about 80%, about 80 to about 85%; and still more preferably the purity is about 85 to about 90%, about 90 to about 95%, and about 95 to about 100%. Purity of female germline stem cells can be determined according to the genetic marker profile within a population. Dosages can be readily adjusted by those skilled in the art (e.g., a decrease in purity may require an increase in dosage).

The skilled artisan can readily determine the amount of cells and optional additives, vehicles, and/or carrier in compositions and to be administered in methods of the invention. Typically, any additives (in addition to the active stem cell(s) and/or agent(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, still more preferably about 0.0001 to about 0.05 wt % or about 0.001 to about 20 wt %, preferably about 0.01 to about 10 wt %, and still more preferably about 0.05 to about 5 wt %. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

III. Oocyte Production

In one embodiment, the present invention provides a method for oocyte production, comprising providing a peripheral blood derived female germline stem cell, or its progenitor, to a female subject, and more preferably to the ovary of said subject, wherein the cell engrafts into the a tissue of the subject (e.g., ovary) and differentiates into an oocyte.

Preferably, the engrafted cells undergo folliculogenesis, wherein the cells differentiate into an oocyte within a follicle. Folliculogenesis is a process in which an ovarian structure consisting of a single oocyte is surrounded by somatic (granulosa without or with theca-interstitial) cells. Somatic cells of the gonad enclose individual oocytes to form follicles. Each fully formed follicle is enveloped in a complete basement membrane. Although some of these newly formed follicles start to grow almost immediately, most of them remain in the resting stage until they either degenerate or some signal(s) activate(s) them to enter the growth phase. A method of the invention can induce ovarian folliculogenesis by providing a peripheral blood derived female germline stem cell, or its progenitor, to the ovary by any one of several routes of administration. The peripheral blood derived female germline stem cell, or its progenitor, can engraft into the ovary and differentiate into an oocyte within a follicle of the ovary.

The number of peripheral blood derived female germline stem cells, or their progenitor cells can be increased by increasing the survival or proliferation of existing peripheral blood derived female germline stem cells, or their progenitor cells.

Agents (e.g., expansion agents) which increase proliferation or survival of peripheral blood derived female germline stem cells, or progenitors derived from peripheral blood derived female germline stem cells, include, but are not limited to, a hormone or growth factor (e.g., a IGF, TGF, BMP, Wnt protein or FGF), a cell-signaling molecule (e.g., S1P or RA), or a pharmacological or pharmaceutical compound (e.g., an inhibitor of GSK-3, an inhibitor of apoptosis such as a Bax inhibitor or caspase inhibitor, an inhibitor of nitric oxide production, or an inhibitor of HDAC activity).

Agents comprising growth factors are known in the art to increase proliferation or survival of stem cells. For example, U.S. Pat. Nos. 5,750,376 and 5,851,832 describe methods for the in vitro culture and proliferation of neural stem cells using TGF. An active role in the expansion and proliferaion of stem cells has also been described for BMPs (Zhu, G. et al, (1999) Dev. Biol. 215: 118-29 and Kawase, E. et al, (2001) Development 131: 1365) and Wnt proteins (Pazianos, G. et al, (2003) Biotechniques 35: 1240 and Constantinescu, S. (2003) J. Cell Mol. Med. 7: 103). U.S. Pat. Nos. 5,453,357 and 5,851,832 describe proliferative stem cell culture systems that utilize FGFs. The contents of each of these references are specifically incorporated herein by reference for their description of expansion agents known in the art.

Agents comprising growth factors are also known in the art to increase mobilization of stem cells from the bone marrow or ovary into the peripheral blood. Mobilizing agents include but are not limited to GCSF or GMCSF. An agent that increases mobilization of stem cells into the blood can be provided before peripheral blood harvest or alternatively, to augment or supplement other methods of the invention where it would be desirable to increase circulating levels of female germline stem cells (e.g., to increase targeting of the cells to the ovary).

Agents comprising cell-signaling molecules are also known in the art to increase proliferation or survival of stem cells. For example, Sphingosine-1-phosphate is known to induce proliferation of neural progenitor cells (Harada, J. et al, (2004) J. Neurochem. 88: 1026). U.S. Patent Application No. 20030113913 describes the use of retinoic acid in stem cell self renewal in culture. The contents of each of these references are specifically incorporated herein by reference for their description of expansion agents known in the art.

Agents comprising pharmacological or pharmaceutical compounds are also known in the art to increase production or survival of stem cells. For example, inhibitors of glycogen synthase kinase maintain pluripotency of embryonic stem cells through activation of Wnt signaling (Sato, N. et al, (2004) Nat. Med. 10: 55). Inhibitors of apoptosis (Wang, Y. et al, (2004) Mol. Cell. Endocrinol. 218: 165), inhibitors of nitric oxide/nitric oxide synthase (Matarredona, E. R. et al, (2004) Brain Res. 995: 274) and inhibitors of histone deacetylases (Lee, J. H. et al, (2004) Genesis 38: 32) are also known to increase proliferation and/or pluripotency. For example, the peptide humanin is an inhibitor of Bax function that suppresses apoptosis (Guo, B. et al, (2003) Nature 423: 456). The contents of each of these references are specifically incorporated herein by reference for their description of expansion agents known in the art.

Oocyte production can be further increased by contacting compositions comprising peripheral blood derived female germline stem cells, or progenitors derived from peripheral blood derived female germline stem cells, with an agent that differentiates peripheral blood derived female germline stem cells or their progenitors into oocytes (e.g., differentiation agents). Such differentiation agents include, but are not limited to, a hormone or growth factor (e.g., TGF, BMP, Wnt protein, SCF or LIF), a signaling molecule (e.g., meiosis-activating sterol, "FF-MAS"), or a pharmacologic or pharmaceutical agent (e.g., a modulator of Id protein function or Snail/Slug transcription factor function).

Agents comprising growth factors are known in the art to differentiate stem cells. For example, TGF-β can induce differentiation of hematopoietic stem cells (Ruscetti, F. W. et al, (2001) Int. J. Hematol. 74: 18). U.S. Patent Application No. 2002142457 describes methods for differentiation of cardiomyocytes using BMPs. Pera et al describe human embryonic stem cell differentiation using BMP-2 (Pera, M. F. et al, (2004) J. Cell Sci. 117: 1269). U.S. Patent Application No. 20040014210 and U.S. Pat. No. 6,485,972 describe methods of using Wnt proteins to induce differentiation. U.S. Pat. No. 6,586,243 describes differentiation of dendritic cells in the presence of SCF. U.S. Pat. No. 6,395,546 describes methods for generating dopaminergic neurons in vitro from embryonic and adult central nervous system cells using LIF. The contents of each of these references are specifically incorporated herein by reference for their description of differentiation agents known in the art.

Agents comprising signaling molecules are also known to induce differentiation of oocytes. FF-Mas is known to promote oocyte maturation (Marin Bivens, C. L. et al, (2004)

BOR papers in press). The contents of each of these references are specifically incorporated herein by reference for their description of differentiation agents known in the art.

Agents comprising pharmacological or pharmaceutical compounds are also known in the art to induce differentiation of stem cells. For example, modulators of Id are involved in hematopoietic differentiation (Nogueria, M. M. et al, (2000) 276: 803) and Modulators of Snail/Slug are known to induce stem cell differentiation (Le Douarin, N. M. et al, (1994) Curr. Opin. Genet. Dev. 4: 685-695; Plescia, C. et al, (2001) Differentiation 68: 254). The contents of each of these references are specifically incorporated herein by reference for their description of differentiation agents known in the art.

The present invention also provides methods for reducing peripheral blood derived female germline stem cells, or their progenitor cells, in vivo, ex vivo or in vitro, comprising contacting peripheral blood derived female germline stem cells or their progenitor cells with an agent that reduces cell proliferation, inhibits cell survival or promotes cell death. Unwanted proliferation of the cells of the invention can give rise to cancerous and pre-cancerous phenotypes (e.g., germ cell tumors, ovarian cancer, testicular cancer). Such methods can be used to control unwanted proliferation (e.g., cancer) or for contraceptive measures by reducing the numbers of germline stem cells, and optionally their progenitors or oocytes.

Agents that reduce cell proliferation include, but are not limited to, a hormone or growth factor (e.g., TGF-$\beta$), a peptide antagonist of mitogenic hormones or growth factors (e.g., the BMP antagonists, PRDC and Gremlin), or a pharmacological or pharmaceutical compound (e.g., a cell cycle inhibitor, or an inhibitor of growth factor signaling).

Agents that inhibit cell survival include, but are not limited to, a hormone, growth factor or cytokine (e.g., a pro-apoptotic TNF super family member such as TNF-$\alpha$, FasL and TRAIL), an antagonist of pro-survival Bcl-2 family member function, a signaling molecule (e.g., a ceramide), or a pharmacological or pharmaceutical compound (e.g., an inhibitor of growth factor signaling). Pro-survival Bcl-2 family members include Bcl-2, Bcl-xl (Cory, S, and Adams, J. M. (2000) Nat Rev Cancer 2(9):647-656; Lutz, R. J. (2000) Cell Survival Apoptosis 28:51-56), Bcl-W (Gibson, L., et al. (1996) Oncogene 13, 665-675; Cory, S, and Adams, J. M. (2000) Nat Rev Cancer 2(9):647-656), Mcl-1 (Kozopas, K. M., et al. (1993) Proc. Natl. Acad. Sci. U.S.A. 90:3516-3520; Reynolds, J. E., et al. (1994) Cancer Res. 54:6348-6352; Cory, S, and Adams, J. M. (2000) Nat Rev Cancer 2(9):647-656) and A1 (Cory, S, and Adams, J. M. (2000) Nat Rev Cancer 2(9):647-656; Gonzales, J., et al. (2003) Blood 101(7):2679-2685; Reed, J. C. (1997) Nature 387:773-776).

Agents that promote cell death include, but are not limited to, a pro-apoptotic tumor necrosis factor superfamily member (e.g., TNF-$\alpha$, FasL and TRAIL), agonist of pro-apoptotic Bcl-2 family member function and ceramide. Pro-apoptotic Bcl-2 family members include Bax (Oltvai, Z N, et al. (1993): Cell 74: 609-619), Bak (Chittenden, T, et al. (1995) Nature 374:733-736), Bid (Luo, X., et al. (1998) Cell 94:481-490), Hrk (Inohara, N. et al. (1997) EMBO J. 16(7):1686-1694), Bod (Hsu, et al. (1998) Mol Endocrinol. 12(9):1432-1440), Bim (O'Connor, L., et al. (1998) EMBO J. 17(2):385-395), Noxa (Oda, E., et al. (2000) Science 288, 1053-1058; Yakovlev, A. G., et al. (2004) J Biol Chem 279(27):28367-28374), puma (Nakano, K. and Vousden, K. H. (2001) Mol Cell 7(3): 683-694), Bok (Yakovlev, A. G., et al. (2004) J Biol Chem 279(27):28367-28374; Hsu, S Y, et al. (1997) Proc Natl Acad Sci USA. 94(23):12401-6) and Bcl-xs (Boise, L. H., et al. (1993) Cell 74:597-608).

Several agents are known in the art to inhibit cell proliferation or survival or promote cell death, including PRDC (Sudo et al, (2004) J. Biol. Chem., advanced publication), TNF (Wong, G. et al, (2004) Exp. Neurol. 187: 171), FasL (Sakata, S. et al, (2003) Cell Death Differ. 10: 676) and TRAIL (Pitti, R M, et al. (1996) J Biol Chem 271: 12687-12690; Wiley, S R, et al. (1995) Immunity 3: 673-682). Ceramide mediates the action of tumor necrosis factor on primitive human hematopoietic cells (Magruer-Satta, V. et al, (2000) Blood 96: 4118-23). Agonist/antagonist of Bcl-2 family members, such as Bcl-2, Bcl-XL, Bcl-W, Mcl-1, A1, Bax, Bak, Bid, Hrk, Bod, Bim, Noxa, Puma, Bok and Bcl-xs, are known to inhibit stem cell survival (Lindsten, T. et al, (2003) J. Neurosci. 23: 11112-9). Agents comprising pharmacological or pharmaceutical compounds are also known in the art to inhibit cell survival. For example, inhibitors of growth factor signaling, such as QSulfl, a heparan sulfate 6-O-endosulfatase that inhibits fibroblast growth factor signaling, can inhibit stem cell survival (Wang, S. et al, (2004) Proc. Natl. Acad. Sci. USA 101: 4833). The contents of each of these references are specifically incorporated herein by reference for their description of agents known in the art to inhibit cell survival.

Agents can be provided directly to the reproductive organ of interest. Alternatively, agents can be provided indirectly to the reproductive organ of interest, for example, by administration into the circulatory system.

Agents can be administered to subjects in need thereof by a variety of administration routes. Methods of administration, generally speaking, may be practiced using any mode of administration that is medically acceptable, meaning any mode that produces effective levels of the active compounds without causing clinically unacceptable adverse effects. Such modes of administration include oral, rectal, topical, intraocular, buccal, intravaginal, intracisternal, intracerebroventricular, intratracheal, nasal, transdermal, within/on implants, e.g., fibers such as collagen, osmotic pumps, or grafts comprising appropriately transformed cells, etc., or parenteral routes. The term "parenteral" includes subcutaneous, intravenous, intramuscular, intraperitoneal, intragonadal or infusion. Intravenous or intramuscular routes are not particularly suitable for long-term therapy and prophylaxis. A particular method of administration involves coating, embedding or derivatizing fibers, such as collagen fibers, protein polymers, etc. with therapeutic proteins. Other useful approaches are described in Otto, D. et al., J. Neurosci. Res. 22: 83 and in Otto, D. and Unsicker, K. J. Neurosci. 10: 1912.

In vitro and ex vivo applications can involve culture of the peripheral blood derived female germline stem cells or their progenitors with the selected agent to achieve the desired result. Cultures of cells (from the same individual and from different individuals) can be treated with differentiation agents of interest to stimulate the production of oocytes, which can then be used for a variety of therapeutic applications (e.g., in vitro fertilization, implantation).

Differentiated cells derived from cultures of the invention can be implanted into a host. The transplantation can be autologous, such that the donor of the stem cells from which organ or organ units are derived is the recipient of the engineered tissue. The transplantation can be heterologous, such that the donor of the stem cells from which organ or organ units are derived is not that of the recipient of the engineered-tissue. Once transferred into a host, the differentiated cells the function and architecture of the native host tissue.

Peripheral blood derived germline stem cells and the progeny thereof can be cultured, treated with agents and/or administered in the presence of polymer scaffolds. Polymer scaffolds are designed to optimize gas, nutrient, and waste exchange by diffusion. Polymer scaffolds can comprise, for example, a porous, non-woven array of fibers. The polymer scaffold can be shaped to maximize surface area, to allow adequate diffusion of nutrients and growth factors to the cells. Taking these parameters into consideration, one of skill in the art could configure a polymer scaffold having sufficient surface area for the cells to be nourished by diffusion until new blood vessels interdigitate the implanted engineered-tissue using methods known in the art. Polymer scaffolds can comprise a fibrillar structure. The fibers can be round, scalloped, flattened, star-shaped, solitary or entwined with other fibers. Branching fibers can be used, increasing surface area proportionately to volume.

Unless otherwise specified, the term "polymer" includes polymers and monomers that can be polymerized or adhered to form an integral unit. The polymer can be non-biodegradable or biodegradable, typically via hydrolysis or enzymatic cleavage. The term "biodegradable" refers to materials that are bioresorbable and/or degrade and/or break down by mechanical degradation upon interaction with a physiological environment into components that are metabolizable or excretable, over a period of time from minutes to three years, preferably less than one year, while maintaining the requisite structural integrity. As used in reference to polymers, the term "degrade" refers to cleavage of the polymer chain, such that the molecular weight stays approximately constant at the oligomer level and particles of polymer remain following degradation.

Materials suitable for polymer scaffold fabrication include polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, teflon RTM, nylon silicon, and shape memory materials, such as polystyrene-block-butadiene), polynorbornene, hydrogels, metallic alloys, and oligo($\epsilon$-caprolactone)diol as switching segment/oligo(p-dioxyanone)diol as physical crosslink. Other suitable polymers can be obtained by reference to The Polymer Handbook, 3rd edition (Wiley, N.Y., 1989).

Factors, including but not limited to nutrients, growth factors, inducers of differentiation or de-differentiation, products of secretion, immunomodulators, inhibitors of inflammation, regression factors, hormones, or other biologically active compounds can be incorporated into or can be provided in conjunction with the polymer scaffold.

Agents of the invention may be supplied along with additional reagents in a kit. The kits can include instructions for the treatment regime or assay, reagents, equipment (test tubes, reaction vessels, needles, syringes, etc.) and standards for calibrating or conducting the treatment or assay. The instructions provided in a kit according to the invention may be directed to suitable operational parameters in the form of a label or a separate insert. Optionally, the kit may further comprise a standard or control information so that the test sample can be compared with the control information standard to determine if whether a consistent result is achieved.

IV. Spermatogenesis

Methods of the present invention can be used in the production of other reproductive cell types. Accordingly, in one embodiment, the present invention provides a method for restoring or enhancing spermatogenesis, comprising providing a peripheral blood derived male germline stem cell, or its progenitor, to the testes of a male subject, wherein the cell engrafts into the seminiferous epithelium and differentiates into a sperm cell. Administration of a peripheral blood derived male germline stem cell, or its progenitor, to the testes is preferably carried out by testicular injection. Direct injection into the testes advantageously circumvents the blood barrier, and provides cells to suitable locations, such as the seminiferous epithelium.

Spermatogenesis can be further increased by contacting compositions comprising peripheral blood derived male germline stem cells, or progenitors derived from peripheral blood derived male germline stem cells, with an agent that increases the differentiation of peripheral blood derived male germline stem cells or their progenitors into oocytes (e.g., differentiation agents). Such differentiation agents can be, but are not limited to, those described herein.

Spermatogenesis, or the formation of spermatocytes from spermatogonia, can be regulated by numerous factors. Regulators of apoptosis, including Bax, $Bcl_{XL}$, family members, and caspase family members, can modulate spermatogenesis and affect male fertility (Said, T. M., et al. (2004) Hum. Reprod. Update 10: 39-51; Yan, W. et al, (2003) Mol. Endocrinol. 17: 1868). Caspases have been implicated in the pathogenesis of multiple andrological pathologies, such as, inter alia, impaired spermatogenesis, decreased sperm motility, and increased levels of sperm DNA fragmentation. Caspase inhibitors, such as survivin and FLIP, can be used to regulate apoptotic events during spermatogenesis (Weikert S., (2004) Int. J. Androl. 27: 161; Giampietri, C. et al, (2003) Cell Death Differ. 10: 175). Similarly, Bax inhibitors such as humanin, are also implicated in spermatogenic apoptosis (Guo, B. et al., (2003) Nature 423: 456).

Growth factors, such as fibroblast growth factor-4 (Hirai, K. et al, (2004) Exp. Cell Res. 294: 77) can also influence spermatogenesis. FGF-4 can play a critical role as a survival factor for germ cells by protecting them from apoptosis. Upon FGF-4 stimulation in Sertoli cells, lactate production was induced, which is indispensable for germ cell survival. FGF-4 stimulation can also reduce DNA fragmentation in Sertoli cells.

Bone morphogenetic protein (BMP) signaling pathways have also been implicated in maintenance of germ line stem cells in *Drosophila* (Kawase, E. et al, (2004) Development 131: 1365-75; Pellegrini, M. et al, (2003) J. Cell Sci. 116: 3363). BMP4 stimulation of cultured spermatogonia can induce Smad-mediated proliferation, as well as differentiation through the c-kit gene. Additionally, BMP signals from somatic cells were shown to be essential for maintaining germline stem cells through repression of the bam expression, indicating that Bmp signals from the somatic cells maintain germline stem cells at least in part, by repressing bam expression in the testis.

Transforming growth factor (TGF) can also repress bam expression in testis. Maintenance and proliferation of germ line stem cells and their progeny depends upon the ability of these cells to transduce the activity of a somatically expressed TGF-β ligand, known in *Drosophila* as the BMP5/8 ortholog Glass Bottom Boat (Shivdasani, A. A. and Ingham, P. W. (2003) Curr. Biol. 13: 2065). TGF-β signaling represses the expression of bam, which is necessary and sufficient for germ cell differentiation, thereby maintaining germ line stem cells and spermatogonia in their proliferative state.

Sphingosine-1-phosphate (S1P) is also known to affect the survival and proliferation of germ line stem cells and spermatogonia. In a study where irradiated testicular tissue was treated with S1P, the numbers of primary spermatocytes and spermatogonia were higher than untreated tissues, indicating that S1p treatment can protect germ line stem cells against cell death induced by radiation.

Glial-derived neurotrophic factor was found to markedly amplify germline stem cells in murine testis (Kubota, H. et al, (2004) Biol. Reprod. April 28 Epub ahead of print). Transplantation analysis demonstrated not only germline stem cells enrichment, but also differentiation from stem cells into sperm (Yomogida, K. et al, (2003) Biol. Reprod. 69: 1303).

The present invention also provides methods for reducing peripheral blood derived male germline stem cells, or their progenitor cells, in vivo, ex vivo or in vitro, comprising contacting peripheral blood derived male germline stem cells or their progenitor cells with an agent that reduces cell proliferation, inhibits cell survival or promotes cell death. Unwanted proliferation of the cells of the invention can give rise to cancerous and pre-cancerous phenotypes (e.g., germ cell tumors). Such methods can be used to control unwanted proliferation (e.g., cancer) or for contraceptive measures by reducing the numbers of germline stem cells, and optionally their progenitors or sperm cells.

Agents that reduce cell proliferation include, but are not limited to, a hormone or growth factor (e.g., TGF-β), a peptide antagonist of mitogenic hormones or growth factors (e.g., the BMP antagonists, PRDC and Gremlin), or a pharmacological or pharmaceutical compound (e.g., a cell cycle inhibitor, or an inhibitor of growth factor signaling).

Agents that inhibit cell survival include, but are not limited to, a hormone, growth factor or cytokine (e.g., a pro-apoptotic TNF super family member such as TNF-α, FasL and TRAIL), an antagonist of pro-survival Bcl-2 family member function, a signaling molecule (e.g., a ceramide), or a pharmacological or pharmaceutical compound (e.g., an inhibitor of growth factor signaling).

Agents that promote cell death include, but are not limited to, a pro-apoptotic tumor necrosis factor superfamily member (e.g., TNF-α, FasL and TRAIL), agonist of pro-apoptotic Bcl-2 family member function and ceramide.

V. Screening Assays

The invention provides methods for identifying modulators, i.e., candidate or test compounds or agents (e.g., proteins, peptides, peptidomimetics, peptoids, small molecules or other drugs) which modulate peripheral blood derived germline stem cells or the progenitors thereof. Agents thus identified can be used to modulate, for example, proliferation, survival and differentiation of a peripheral blood derived germline stem cell or its progenitor e.g., in a therapeutic protocol.

The test agents of the present invention can be obtained singly or using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. (1994) et al., J. Med. Chem. 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al (1994) Angew. Chem. Int. Ed. Engl. 33:2061; and Gallop et al. (1994) J. Med. Chem. 37:1233.

Libraries of compounds may be presented in solution (e.g., Houghten (1992), Biotechniques 13:412-421), or on beads (Lam (1991), Nature 354:82-84), chips (Fodor (1993) Nature 364:555-556), bacteria (Ladner, U.S. Pat. No. 5,223,409), spores (Ladner U.S. Pat. No. 5,223,409), plasmids (Cull et al. (1992) Proc Natl Acad Sci USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222:301-310; Ladner supra.).

Chemical compounds to be used as test agents (i.e., potential inhibitor, antagonist, agonist) can be obtained from commercial sources or can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock (1989) Comprehensive Organic Transformations, VCH Publishers; T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

In one aspect the compounds are organic small molecules, that is, compounds having molecular weight less than 1,000 amu, alternatively between 350-750 amu. In other aspects, the compounds are: (i) those that are non-peptidic; (ii) those having between 1 and 5, inclusive, heterocyclyl, or heteroaryl ring groups, which may bear further substituents; (iii) those in their respective pharmaceutically acceptable salt forms; or (iv) those that are peptidic.

The terra "heterocyclyl" refers to a nonaromatic 3-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring can be substituted by a substituent.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring can be substituted by a substituent.

The term "substituents" refers to a group "substituted" on an alkyl, cycloalkyl, aryl, heterocyclyl, or heteroaryl group at any atom of that group. Suitable substituents include, without limitation, alkyl, alkenyl, alkynyl, alkoxy, halo, hydroxy, cyano, nitro, amino, SO₃H, perfluoroalkyl, perfluoroalkoxy, methylenedioxy, ethylenedioxy, carboxyl, oxo, thioxo, imino (alkyl, aryl, aralkyl), S(O)$_n$alkyl (where n is 0-2), S(O)$_n$ aryl (where n is 0-2), S(O)$_n$heteroaryl (where n is 0-2), S(O)$_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

Combinations of substituents and variables in compounds envisioned by this invention are only those that result in the formation of stable compounds. The term "stable", as used herein, refers to compounds which possess stability sufficient to allow manufacture, and which maintains the integrity of the compound for a sufficient period of time to be useful for the purposes detailed herein (e.g., transport, storage, assaying, therapeutic administration to a subject).

The compounds described herein can contain one or more asymmetric centers and thus occur as racemates and racemic mixtures, single enantiomers, individual diastereomers and diastereomeric mixtures. All such isomeric forms of these compounds are expressly included in the present invention. The compounds described herein can also be represented in multiple tautomeric forms, all of which are included herein. The compounds can also occur in cis- or trans-or E-or Z-double bond isomeric forms. All such isomeric forms of such compounds are expressly included in the present invention.

Test agents of the invention can also be peptides (e.g., growth factors, cytokines, receptor ligands).

Screening methods of the invention can involve the identification of an agent that increases the proliferation or survival of peripheral blood derived germline stem cells or the progenitors thereof. Such methods will typically involve contacting a population of the germline stem or progenitor cells with a test agent in culture and quantitating the number of new stem or progenitor cells produced as a result. Comparison to an untreated control can be concurrently assessed. Where an increase in the number of stem or progenitor cells is detected relative to the control, the test agent is determined to have the desired activity.

In practicing the methods of the invention, it may be desirable to employ a purified population of peripheral blood derived germline stem cells or the progenitors thereof. A purified population of peripheral blood derived germline stem cells or the progenitors thereof have about 50-55%, 55-60%, 60-65% and 65-70% purity. More preferably the purity is about 70-75%, 75-80%, 80-85%; and still more preferably the purity is about 85-90%, 90-95%, and 95-100%.

Increased amounts of peripheral blood derived germline stem cells or the progenitors thereof can also be detected by an increase in gene expression of genetic markers including an Dazl, Stella and Vasa. The level of expression can be measured in a number of way's, including, but not limited to: measuring the mRNA encoded by the genetic markers; measuring the amount of protein encoded by the genetic markers; or measuring the activity of the protein encoded by the genetic markers.

The level of mRNA corresponding to a genetic marker can be determined both by in situ and by in vitro formats. The isolated mRNA can be used in hybridization or amplification assays that include, but are not limited to, Southern or Northern analyses, polymerase chain reaction analyses and probe arrays. One diagnostic method for the detection of mRNA levels involves contacting the isolated mRNA with a nucleic acid molecule (probe) that can hybridize to the mRNA encoded by the gene being detected. The nucleic acid probe is sufficient to specifically hybridize under stringent conditions to mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the genetic markers described herein.

The level of mRNA in a sample can be evaluated with nucleic acid amplification, e.g., by rtPCR (Mullis (1987) U.S. Pat. No. 4,683,202), ligase chain reaction (Barany (1991) Proc. Natl. Acad. Sci. USA 88:189-193), self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the genetic marker being analyzed.

Screening methods of the invention can involve the identification of an agent that increases the differentiation of peripheral blood derived germline stem cells or the progenitors thereof into oocytes. Such methods will typically involve contacting the germline stem or progenitor cells with a test agent in culture and quantitating the number of new oocytes produced as a result. Comparison to an untreated control can be concurrently assessed. Where an increase in the number of oocytes is detected relative to the control, the test agent is determined to have the desired activity. The test agent can also be assayed using a biological sample (e.g., ovarian tissue); subsequent testing using a population of stem or progenitor cells may be conducted to distinguish the functional activity of the agent (e.g., differentiation rather then increase in proliferation or survival) where the result is ambiguous.

Increased amounts of oocytes be detected by a decrease in gene expression of stem or progenitor genetic markers including an Dazl, Stella and Vasa or an increase in oocyte markers, such as HDAC6, GDF9 and ZP3.

Screening methods of the invention can involve the identification of an agent that decreases the proliferation or survival of peripheral blood derived germline stem cells or the progenitors thereof. Such methods will typically involve contacting a population of the stem or progenitor cells, or a biological sample (e.g., ovarian tissue) with a test agent in culture and quantitating the number of stem or progenitor cells lost as a result. Comparison to an untreated control can be concurrently assessed. Where a decrease in the number of stem or progenitor cells is detected relative to the control, the test agent is determined to have the desired activity.

VI. Methods of Treatment and Diagnosis

Peripheral blood derived germline stem cells of the invention or their progenitors can be used in a variety of therapeutic applications (e.g., oocyte generation for in vivo restoration or ex vivo procedures including in vitro fertilization and somatic cell nuclear transfer). Accordingly, methods of the invention relate to, among other things, the use of peripheral blood derived germline stem cells, or their progenitor cells, to provide genii cells in the treatment of reproductive disorders.

Thus, the present invention provides methods for treating infertility comprising providing a peripheral blood derived female germline stem cell, or its progenitor, to a female subject in need thereof, wherein the cell engrafts into a tissue and differentiates into an oocyte, which can later be provided for fertilization (e.g., following ovulation or in vitro fertilization in the subject). Preferably, the tissue is ovarian tissue, however, other tissues in the body may host the engrafted cell that in turn generates an oocyte. Oocytes harbored in extra-ovarian tissues can be harvested and used for procedures including in vitro fertilization.

The present invention also provides methods for treating infertility comprising administering an agent that increases the production or survival of peripheral blood derived female germline stem cells or their progenitors. Such agents may also promote cell proliferation or survival, thereby enhancing oocyte production.

Agents can be provided directly to the reproductive organ of interest. Alternatively, agents can be provided indirectly to the reproductive organ of interest, for example, by administration into the circulatory system.

The present invention also provides methods for repairing damaged ovarian tissue, comprising providing a peripheral blood derived female germline stem cell, or its progenitor, to the ovarian tissue, wherein the cell engrafts into the ovarian tissue and differentiates into an oocyte. Except where expressly stated herein, the ovarian tissue was not damaged by chemotherapy or radiotherapy.

Damage can be caused, for example, by exposure to cytotoxic factors, hormone deprivation, growth factor deprivation, cytokine deprivation, cell receptor antibodies, and the like. Where damage may be caused by an anticipated course of chemotherapy and/or radiotherapy, administration of an agent that protects against reproductive injury prior to or concurrently with chemotherapy and/or radiotherapy can protect fertility and enhance the restoration methods described herein. The protective agent can include but is not limited to S1p, Bax, or any agent that increases SDF-1 activity (i.e., SDF-1 mediated migration and homing of stem cells). For a description of the use of SIP in protecting reproductive systems, see U.S. application Ser. No. 10/217,259, filed on Aug. 12, 2002 and published as 20030157086 on Aug. 21, 2003, the contents of which are herein incorporated by reference.

The present invention also provides methods for restoring ovarian function in a menopausal female subject, comprising providing a peripheral blood derived female germline stem cell, or its progenitor, to the subject, wherein the cell engrafts into the ovary and differentiates into an oocyte. The menopausal female subject can be in a stage of either peri- or post-menopause, with said menopause caused by either normal (e.g., aging) or pathological (e.g., surgery, disease, ovarian damage) processes.

Ovarian function in a post-menopausal female can also be restored by administering an an agent that increases the amount of peripheral blood derived female germline stem cells or their progenitors and/or their differentiation into oocytes (e.g., by increasing the number or life span of peripheral blood derived female germline stem cells, as well as by increasing the differentiation of peripheral blood derived female germline stem cells into oocytes).

Restoration of ovarian function can relieve adverse symptoms and complications associated with menopausal disorders, including, but not limited to, somatic disorders such as osteoporosis, cardiovascular disease, somatic sexual dysfunction, hot flashes, vaginal drying, sleep disorders, depression, irritability, loss of libido, hormone imbalances, and the like, as well as cognitive disorders, such as loss of memory; emotional disorders, depression, and the like.

Peripheral blood derived germline stem cells of the invention, their progenitors or their in vitro-derived progeny, can be administered as previously described, and obtained by all methods known in the art.

Peripheral blood can be isolated by standard methods known in the art, which include methods for harvesting umbilical cord blood. In general, peripheral blood mononuclear cells (PBMCs) are taken from a patient using standard techniques. By "peripheral blood mononuclear cells" or "PBMCs" herein is meant lymphocytes (including T-cells, B-cells, NK cells, etc.) monocytes and stem cells. In some embodiments of the invention, only PBMCs are taken, either leaving or returning red blood cells and polymorphonuclear leucocytes to the patient. This is done as is known in the art, for example using leukophoresis techniques. In general, a 5 to 7 liter leukophoresis step it done, which essentially removes PBMCs from a patient, returning the remaining blood components. Collection of the cell sample is preferably done in the presence of an anticoagulant such as heparin, as is known in the art.

In general, the sample comprising the PBMCs can be pretreated in a wide variety of ways. Generally, once collected, the cells can be additionally concentrated, if this was not done simultaneously with collection or to further purify and/or concentrate the cells. The cells may be washed, counted, and resuspended in buffer transferred to a sterile, closed system for further purification and activation.

The PBMCs are generally concentrated for treatment, using standard techniques in the art in a preferred embodiment, the leukophoresis collection step results in a concentrated sample of PBMCs, in a sterile leukopak, that may contain reagents or doses of the suppressive composition, as is more fully outlined below. Generally, an additional concentration/purification step is done, such as Ficoil-Hypaque density gradient centrifugation as is known in the art. Separation or concentration procedures include but are not limited to magnetic separation, using antibody-coated magnetic beads, affinity chromatography, cytotoxic agents, either joined to a monoclonal antibody or used with complement, "panning", which uses a monoclonal antibody a to a solid matrix. Antibodies attached to solid matrices, such as magnetic beads, agarose beads, polystyrene beads, follow fiber membranes and plastic surfaces, allow for direct separation. Cells bound by, antibody can be removed or concentration by physically separating the solid support from the cell suspension. The exact conditions a and procedure depend on factors specific to the system employed. The selection of appropriate conditions is well within the skill in the art.

Antibodies may be conjugated to biotin, which then can be removed with avidin or streptavidin bound to a support, or fluorochromes, which can be used with a fluorescence activated cell sorter (FACS), to enable cell separation. Any technique may be employed as long as it is not detrimental to the viability of the desired cells.

In a preferred embodiment, the PBMCs are separated in a automated, closed system such as the Nexell Isolex 300i Magnetic Cell Selection System. Generally, this is done to maintain sterility and to insure standardization of the methodology used for cell separation, activation and development of suppressor cell function.

Once purified or concentrated the cells may be aliquoted and frozen, preferably, in liquid nitrogen or used immediately as described below. Frozen cells may be thawed and used as needed. Cryoprotective agents, which can be used, include but are not limited to dimethyl sulfoxide (DMSO) (Lovelock, J. E. and Bishop, M. W. H., 1959, Nature 183:1394-1395; Ashwood-Smith, M. J., 1961, Nature 190:1204-1205), hetastarch, glycerol, polyvinylpyrrolidine (Rinfret, A. P., 1960, Ann. N.Y. Acad. Sci. 85:576), polyethylene glycol (Sloviter, H. A. and Ravdin, R. G., 1962, Nature 196:548), albumin, dextran, sucrose, ethylene glycol, i-erythritol, D-ribitol, D-mannitol (Rowe, A. W., et al., 1962, Fed. Proc. 21:157), D-sorbitol, i-inositol, D-lactose, choline chloride (Bender, M. A., et al., 1960, J. Appl. Physiol. 15:520), amino acids (Phan The Tran and Bender, M. A, 1960, Exp. Cell Res. 20:851), methanol, acetamide, glycerol monoacetate (Lovelock. J. E., 1954, Biochem. J. 56:265), and inorganic salts (Phan The Tran and Bender, M. A., 1960, Proc. Soc. Exp. Biol. Med. 104:388; Phan The Tran and Bender, M. A., 1961, in Radiobiology Proceedings of the Third Australian Conference on Radiobiology, P. L. T., ed., Butterworth, London, p. 59). Typically, the cells may be stored in 10% DMSO, 50% serum, and 40% RPMI 1640 medium. Methods of cell separation and purification are found in U.S. Pat. No. 5,888,499, which is expressly incorporated by reference.

In a preferred embodiment, the PBMCs are then washed to remove serum proteins and soluble blood components, such as autoantibodies, inhibitors, etc., using techniques well known in the art Generally, this involves addition of physiological media or buffer, followed by centrifugation. This may be repeated as necessary. They can be resuspended in physiological media, preferably AIM-V serum free medium (Life Technologies) (since serum contains significant amounts of inhibitors of TGF-β although buffers such as Hanks balanced salt solution (HBBS) or physiological buffered saline (PBS) can also be used.

Generally, the cells are then counted; in general from $1 \times 10^9$ to $2 \times 10^9$ white blood cells are collected from a 5-7 liter leukophoresis step. These cells are brought up roughly 200 mls of buffer or media.

Prior to harvest, patients may be treated with agents known in the art to increase mobilization of stem cells from the bone marrow or ovary into the peripheral blood. Mobilizing agents include but are not limited to GCSF or GMCSF.

Peripheral blood derived germline stem cells of the invention can, if needed, be purified from peripheral blood, including umbilical cord blood. Therefore, peripheral blood derived germline stem cells that can be used in the methods of the invention can comprise a purified sub-population of cells including, but not limited to female and male germline stem cells. Purified cells can be collected and separated, for example, by flow cytometry.

Peripheral blood derived germline stem cells of the invention can be autologous (obtained from the subject) or heterologous (e.g., obtained from a donor). Heterologous cells can be provided together with immunosuppressive therapies known in the art to prevent immune rejection of the cells.

According to methods of the invention, peripheral blood can be harvested during the lifetime of the subject, but a pre-menopausal harvest is recommended. Furthermore, harvest prior to illness (e.g., cancer) is desirable, and harvest prior to treatment by cytotoxic means (e.g., radiation or chemotherapy) will improve yield and is therefore also desirable. For increased yield from female donors, it may be desirable to coordinate isolation with appropriate stages of the female reproductive cycle that exhibit higher levels of female germline stem cells in the peripheral blood, as described in Example 4.

In some embodiments, it is beneficial to quantify the number of female germline stem cells or their progenitors present in a sample of peripheral blood. Where the amount of female germline stem cells or their progenitors in a subject is substantially reduced (e.g., less than 100) in comparison to that of a healthy subject, she can have, or be at risk of developing, premature ovarian failure. The quantity of female germline stem cells or their progenitors circulating in the peripheral blood can be highest during particular stages of the female reproductive cycle. Thus, it may be desirable to coordinate the timing of sample extraction and diagnosis with the timing of such a stage of the female reproductive cycle.

Purified peripheral blood derived female germline stem cells or their progenitors can be obtained by standard methods known in the art, including cell sorting by FACs. Isolated peripheral blood can be sorted using flow cytometers known in the art (e.g., a BD Biosciences FACScalibur cytometer) based on cell surface expression of Sca-1 (van de Rijn et al., (1989) Proc. Natl. Acad. Sci. USA 86, 4634-4638) and/or c-Kit (Okada et al., (1991) Blood 78, 1706-1712); (Okada et al., (1992) Blood 80, 3044-3050) following an initial immunomagnetic bead column-based fractionation step to obtain lineage-depleted (lin⁻) cells (Spangrude et al., (1988) Science 241, 58-62); (Spangrude and Scollay, (1990) Exp. Hematol. 18, 920-926), as described (Shen et al., (2001) J. Immunol. 166, 5027-5033); (Calvi et al., (2003) Nature 425, 841-846).

For serial passage-based enrichment of peripheral blood derived female germline stem cells or their progenitors in-vitro (Meirelles and Nardi, (2003) Br. J. Haematol. 123, 702-711); (Tropel et al., (2004) Exp. Cell Res. 295, 395-406), isolated peripheral blood can be plated on plastic in Dulbecco's modified Eagle's medium (Fisher Scientific, Pittsburgh, Pa.) with 10% fetal bovine serum (Hyclone, Logan, Utah), penicillin, streptomycin, L-glutamine and amphotericin-B. About forty-eight hours after the initial plating, the supernatants containing non-adherent cells can be removed and replaced with fresh culture medium after gentle washing. The cultures can then be maintained and passed once confluence is reached (e.g., for a total of about three times over the span of about 6 weeks) at which time the cultures can be terminated to collect adherent cells for analysis.

Compositions comprising peripheral blood derived germline stem cells or their progenitors can be provided directly to the reproductive organ of interest (e.g., ovary or testes). Alternatively, compositions comprising peripheral blood derived germline stem cells or their progenitors can be provided indirectly to the reproductive organ of interest, for example, by administration into the circulatory system (e.g., to extra-ovarian circulation).

Prior to administration, peripheral blood derived germline stem cells, their progenitors or their progeny, described herein can optionally be genetically modified, in vitro, in vivo or ex vivo, by introducing heterologous DNA or RNA or protein into the cell by a variety of recombinant methods known to those of skill in the art. These methods are generally grouped into four major categories: (1) viral transfer, including the use of DNA or RNA viral vectors, such as retroviruses (including lentiviruses), Simian virus 40 (SV40), adenovirus, Sindbis virus, and bovine papillomavirus, for example; (2) chemical transfer, including calcium phosphate transfection and DEAE dextran transfection methods; (3) membrane fusion transfer, using DNA-loaded membranous vesicles such as liposomes, red blood cell ghosts, and protoplasts, for example; and (4) physical transfer techniques, such as microinjection, electroporation, or direct "naked" DNA transfer.

The peripheral blood derived germline stem cells of the invention, their progenitors or their in progeny, can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids, or PNAs), or by ribozyme technology, for example. The altered genome may contain the genetic sequence of a selectable or screenable marker gene that is expressed so that the cell with altered genome, or its progeny, can be differentiated from cells having an unaltered genome. For example, the marker may be a green, red, yellow fluorescent protein, β-galactosidase, the neomycin resistance gene, dihydrofolate reductase (DHFR), or hygromycin, but are not limited to these examples.

In some cases, the underlying defect of a pathological state is a mutation in DNA encoding a protein such as a metabolic protein. Preferably, the polypeptide encoded by the heterologous DNA lacks a mutation associated with a pathological state. In other cases, a pathological state is associated with a decrease in expression of a protein. A genetically altered peripheral blood derived germline stem cell, or its progeny, may contain DNA encoding such a protein under the control of a promoter that directs strong expression of the recombinant protein. Alternatively, the cell may express a gene that can be regulated by an inducible promoter or other control mechanism where conditions necessitate highly controlled regulation or timing of the expression of a protein, enzyme, or other cell product. Such stem cells, when transplanted into a subject suffering from abnormally low expression of the protein, produce high levels of the protein to confer a therapeutic benefit. For example, the peripheral blood derived germline stem cell of the invention, its progenitor or its in vitro-derived progeny, can contain heterologous DNA encoding genes to be expressed, for example, in gene therapy. Peripheral blood derived germline stem cells of the invention, their progenitors or their in vitro-derived progeny, can contain heterologous DNA encoding Atm, the gene responsible for the human disease Ataxia-telangiectasia in which fertility is disrupted. Providing Atm via peripheral blood derived germline stem cells, their progenitors or their in vitro-derived progeny, can further relieve defects in ovarian function. DNA encoding a gene product that alters the functional properties of peripheral blood derived germline stem cells in the absence of any disease state is also envisioned. For example, delivery of a gene that inhibits apoptosis, or that prevents differentiation would be beneficial.

Insertion of one or more pre-selected DNA sequences can be accomplished by homologous recombination or by viral integration into the host cell genome. The desired gene sequence can also be incorporated into the cell, particularly into its nucleus, using a plasmid expression vector and a nuclear localization sequence. Methods for directing polynucleotides to the nucleus have been described in the art. The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) expression in specific cell compartments (including but not limited to the cell membrane).

Calcium phosphate transfection can be used to introduce plasmid DNA containing a target gene or polynucleotide into isolated or cultured peripheral blood derived germline stem cells or their progenitors and is a standard method of DNA transfer to those of skill in the art. DEAE-dextran transfection, which is also known to those of skill in the art, may be preferred over calcium phosphate transfection where transient transfection is desired, as it is often more efficient. Since the cells of the present invention are isolated cells, microinjection can be particularly effective for transferring genetic material into the cells. This method is advantageous because it provides delivery of the desired genetic material directly to the nucleus, avoiding both cytoplasmic and lysosomal degradation of the injected polynucleotide. This technique has been used effectively to accomplish peripheral blood derived modification in transgenic animals. Cells of the present invention can also be genetically modified using electroporation.

Liposomal delivery of DNA or RNA to genetically modify the cells can be performed using cationic liposomes, which form a stable complex with the polynucleotide. For stabilization of the liposome complex, dioleoyl phosphatidylethanolamine (DOPE) or dioleoyl phosphatidylcholine (DOPQ) can be added. Commercially available reagents for liposomal transfer include Lipofectin (Life Technologies). Lipofectin, for example, is a mixture of the cationic lipid N-[1-(2,3-dioleyloxy)propyl]-N-N-N-trimethyl ammonia chloride and DOPE. Liposomes can carry larger pieces of DNA, can generally protect the polynucleotide from degradation, and can be targeted to specific cells or tissues. Cationic lipid-mediated gene transfer efficiency can be enhanced by incorporating purified viral or cellular envelope components, such as the purified G glycoprotein of the vesicular stomatitis virus envelope (VSV-G). Gene transfer techniques which have been shown effective for delivery of DNA into primary and established mammalian cell lines using lipopolyamine-coated DNA can be used to introduce target DNA into the peripheral blood derived germline stem cells described herein.

Naked plasmid DNA can be injected directly into a tissue mass formed of differentiated cells from the isolated peripheral blood derived germline stem cells or their progenitors. This technique has been shown to be effective in transferring plasmid DNA to skeletal muscle tissue, where expression in mouse skeletal muscle has been observed for more than 19 months following a single intramuscular injection. More rapidly dividing cells take up naked plasmid DNA more efficiently. Therefore, it is advantageous to stimulate cell division prior to treatment with plasmid DNA. Microprojectile gene transfer can also be used to transfer genes into stem cells either in vitro or in vivo. The basic procedure for microprojectile gene transfer was described by J. Wolff in Gene Therapeutics (1994), page 195. Similarly, microparticle injection techniques have been described previously, and methods are known to those of skill in the art. Signal peptides can be also attached to plasmid DNA to direct the DNA to the nucleus for more efficient expression.

Viral vectors are used to genetically alter peripheral blood derived germline stem cells of the present invention and their progeny. Viral vectors are used, as are the physical methods previously described, to deliver one or more target genes, polynucleotides, antisense molecules, or ribozyme sequences, for example, into the cells. Viral vectors and methods for using them to deliver DNA to cells are well known to those of skill in the art. Examples of viral vectors that can be used to genetically alter the cells of the present invention include, but are not limited to, adenoviral vectors, adeno-associated viral vectors, retroviral vectors (including lentiviral vectors), alphaviral vectors (e.g., Sindbis vectors), and herpes virus vectors.

Peptide or protein transfection is another method that can be used to genetically alter peripheral blood derived germline stem cells of the invention and their progeny. Peptides including, but not limited to, Pep-1 (commercially available as Chariot™) and MPG, can quickly and efficiently transport biologically active proteins, peptides, antibodies, and nucleic acids directly into cells, with an efficiency of about 60% to about 95% (Morris, M. C. et al, (2001) Nat. Biotech. 19: 1173-1176). Without wishing to be bound by theory, the peptide forms a non-covalent bond with the macromolecule of interest (i.e., protein, nucleic acid). The binding reaction stabilizes the protein and protects it from degradation. Upon delivery into the cell of interest, such as stem cells of the invention, the peptide-macromolecule complex dissociates, leaving the macromolecule biologically active and free to proceed to its target organelle. Delivery can occur in the presence of absence of serum. Uptake and delivery can occur at 4° C., which eliminates endosomal processing of incoming macromolecules. Movement of macromolecules through the endosomal pathway can modify the macromolecule upon uptake. Peptides such as Pep-1, by directly delivering a protein, antibody, or peptide of interest, bypass the transcription-translation process.

Methods of the invention can provide oocyte reserves for use in ex vivo procedures, such as somatic cell nuclear transfer. Employing recombinant techniques prior to nuclear transfer will allow for the design of customized oocytes and ultimately produce embryos from which embryonic stem cells can be derived. In addition, genetic manipulation of donor DNA prior to nuclear transfer will result in embryos that possess the desired modification or genetic trait.

Methods of somatic cell nuclear transfer are well known in the art. See U.S. application Ser. No. 10/494,074, filed on Mar. 24, 2004 and published as 20050064586; Wilmut et al. (1997) Nature, 385, 810-813; Wakayama, et al. (1998) Nature 394: 369-374; and Teruhiko et al., (1999) PNAS 96:14984-14989. Nuclear transplantation involves the transplantation of donor cells or cell nuclei into enucleated oocytes. Enucleation of the oocyte can be performed in a number of manners well known to those of ordinary skill in the art. Insertion of the donor cell or nucleus into the enucleated oocyte to form a reconstituted cell is usually by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell is typically activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, are typically cultured in medium well known to those of ordinary skill in the art and then transferred to the womb of an animal.

Methods for the generation of embryonic stem cells from embryos are also well known in the art. See Evans, et al. (1981) Nature, 29:154-156; Martin, et al. (1981) PNAS, 78:7634-7638; Smith, et al. (1987) Development Biology, 121:1-9; Notarianni, et al. (1991) J. Reprod. Suppl. 43:255-260; Chen R L, et al. (1997) Biology of Reproduction, 57 (4):756-764; Wianny, et al. (1999) Theriogenology, 52 (2): 195-212; Stekelenburg-Hamers, et al. (1995) Mol. Reprod. 40:444-454; Thomson, et al. (1995) PNAS, 92 (17):7844-8 and Thomson (1998) Science, 282 (6):1145-1147. Accordingly, embryos produced from oocytes of the invention can be genetically modified, either through manipulation of the oocyte in vitro prior to fertilization or manipulation of donor DNA prior to nuclear transfer into the enucleated oocyte, to produce embryos having a desired genetic trait.

VII. In Vitro Fertilization

Oocytes produced from peripheral blood derived female germline stem cells of the invention, or progenitors derived from peripheral blood derived female germline stem cells of the invention, as described herein can also be used for methods of in vitro fertilization. Accordingly, the invention provides methods for in vitro fertilization of a female subject, comprising the steps of:

a) producing an oocyte by culturing a peripheral blood derived female germline stem cell, or its progenitor, in the presence of an oocyte differentiation agent;

b) fertilizing the oocyte in vitro to form a zygote;

c) implanting the zygote into the uterus of a female subject.

Methods of in vitro fertilization are well known in the art, and are now rapidly becoming commonplace. Couples are generally first evaluated to diagnose their particular infertility problem(s). These may range from unexplained infertility of both partners to severe problems of the female (e.g., endometriosis resulting in nonpatent oviducts with irregular menstrual cycles or polycystic ovarian disease) or the male (e.g., low sperm count with morphological abnormalities, or an inability to ejaculate normally as with spinal peripheral lesions, retrograde ejaculation, or reversed vasectomy). The results of these evaluations also determine the specific procedure to be performed for each couple.

Procedures often begin with the administration of a drug to down-regulate the hypothalamic/pituitary system (LHRH agonist). This process decreases serum concentrations of the gonadotropins, and developing ovarian follicles degenerate, thereby providing a set of new follicles at earlier stages of development. This permits more precise control of the maturation of these new follicles by administration of exogenous gonadotropins in the absence of influences by the hypothalamic pituitary axis. The progress of maturation and the number of growing follicles (usually four to ten stimulated per ovary) are monitored by daily observations using ultrasound and serum estradiol determinations. When the follicles attain preovulatory size (18-21 mm) and estradiol concentrations continue to rise linearly, the ovulatory response is initiated by exogenous administration of human chorionic gonadotropins (hCG).

Oocytes can be obtained from peripheral blood derived female germline stem cells, or progenitors derived from peripheral blood derived female germline stem cells, as previously described herein. Peripheral blood derived female germline stem cells, or progenitors derived from peripheral blood derived female germline stem cells, can be cultured in the presence of an oocyte differentiation agent which induces differentiation into oocytes. The differentiation agent can be supplied exogenously (e.g., added to the culture medium) or from endogenous sources during co-culture with allogenic or heterogenic ovarian tissue. Peripheral blood derived female germline stem cells of the invention can also be cultured in a tissue-engineered structure wherein the differentiation agent is either exogenously or endogenously supplied and oocytes are obtained.

Individual oocytes can be evaluated morphologically and transferred to a petri dish containing culture media and heat-inactivated serum. A semen sample is provided by the male partner and processed using a "swim up" procedure, whereby the most active, motile sperm will be obtained for insemination. If the female's oviducts are present, a procedure called GIFT (gamete intrafallopian transfer) can be performed at this time. By this approach, oocyte-cumulus complexes surrounded by sperm are placed directly into the oviducts by laproscopy. This procedure best simulates the normal sequences of events and permits fertilization to occur within the oviducts. Not surprisingly, GIFT has the highest success rate with 22% of the 3,750 patients undergoing ova retrieval in 1990 having a live delivery. An alternative procedure ZIFT (zygote intrafallopian transfer) permits the selection of in vitro fertilized zygotes to be transferred to oviducts the day following ova retrieval. Extra zygotes can be cryopreserved at this time for future transfer or for donation to couples without female gametes. Most patients having more serious infertility problems, however, will require an additional one to two days incubation in culture so that preembryos in the early cleavage states can be selected for transfer to the uterus. This IVF-UT (in vitro fertilization uterine transfer) procedure entails the transcervical transfer of several 2-6 cell (day 2) or 8-16 (day 3) preembryos to the fundus of the uterus (4-5 preembryos provides optimal success).

Procedures for in vitro fertilization are also described in U.S. Pat. Nos., 6,610,543 6,585,982, 6,544,166, 6,352,997, 6,281,013, 6,196,965, 6,130,086, 6,110,741, 6,040,340, 6,011,015, 6,010,448, 5,961,444, 5,882,928, 5,827,174, 5,760,024, 5,744,366, 5,635,366, 5,691,194, 5,627,066, 5,563,059, 5,541,081, 5,538,948, 5,532,155, 5,512,476, 5,360,389, 5,296,375, 5,160,312, 5,147,315, 5,084,004, 4,902,286, 4,865,589, 4,846,785, 4,845,077, 4,832,681, 4,790,814, 4,725,579, 4,701,161, 4,654,025, 4,642,094, 4,589,402, 4,339,434, 4,326,505, 4,193,392, 4,062,942, and 3,854,470, the contents of which are specifically incorporated by reference for their description of these procedures.

The following examples are put forth for illustrative purposes only, and are not intended to limit the scope of what the inventors regard as their invention.

EXAMPLES

Example 1

Female Germline Stem Cells in Peripheral Blood

It has recently been determined that bone marrow serves as a germline stem cell reservoir for the maintenance of oocyte production in adult females. See U.S. application Ser. No. 11/131,153, filed on May 17, 2005, the contents of which are herein incorporated by reference. It was therefore proposed that germline stem cell-derived progeny utilize the peripheral blood supply as a conduit for travel to the ovaries. As shown herein, peripheral blood contains germline stem cells and thus, peripheral blood cell transplantation (PBCT) can be used to rescue oocyte production in female recipients.

For the first of these experiments, a doxorubicin insult model was utilized, in which there occurs a rapid and spontaneous regeneration of the primordial follicle pool following doxorubicin insult, presumably through germline stem cell-derived progeny arriving to the ovaries via the general circulation. Accordingly, such a model lends itself well to rapidly assessing the contribution of peripheral blood-derived germ cells to de-novo oocyte production in adult females.

To distinguish between those new oocytes derived from the host versus the donor, peripheral blood mononuclear cells were collected from adult transgenic female mice with ubiquitous expression of green fluorescent protein (GFP). For PBCT, peripheral blood was collected and layered on Ficoll-Paque Plus (Amersham Biosciences). The samples were centrifuged at 800×g for 15 minutes at 4 C, and mononuclear cells were collected from the Ficoll-buffer interface. After collection, the cells were washed and resuspended in PBS at a final concentration of $3\text{-}6 \times 10^6$ cell $ml^1$. Recipient adult (6-7 weeks of age) wild-type female mice were injected with doxorubicin (5 mg $kg^{-1}$), followed by PBCT (0.5 ml of cells per mouse, via the tail vein) 25 hours later. Twenty-four hours after PBCT, ovaries were collected and analyzed for GFP expression by immunohistochemistry.

Figures 1D, 1E, 1F:
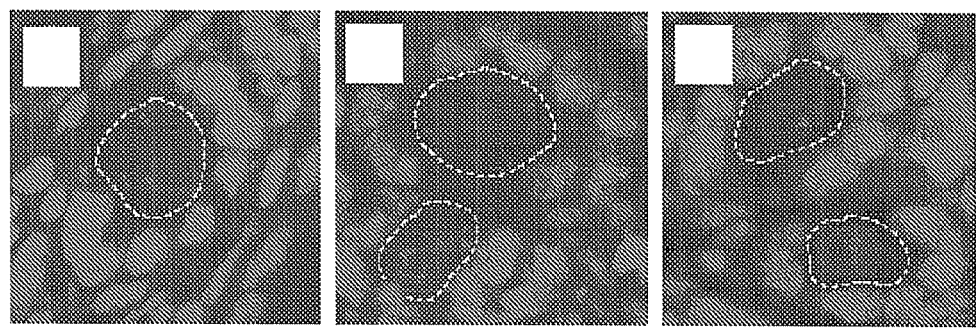
FIG. 1F shows GFP-negative oocytes in the same ovaries as those shown in FIGS. C-E.

As controls for the experiment, GFP expression was detectable in primordial and primary oocytes of transgenic females (FIG. 1a) but was not observed in oocytes of wild-type females prior to PBCT (FIG. 1b). However, primordial and early primary follicles with GFP-positive oocytes were detected in the ovaries of adult wild-type female mice within 24 hours of PBCT (FIG. 1c-e). As expected, GFP-negative primordial and primary oocytes were also found in the same ovaries of mice receiving PBCT (FIG. 1f), representing either those oocytes not destroyed by doxorubicin treatment or new oocytes formed from host germline stem cell-derived progeny following the insult.

Next, transgenic female mice with GFP expression driven by an 18-kb fragment of the Oct4 promoter in which the proximal enhancer region has been inactivated (GOF18-ΔPE or TgOG2) (Yeom et al., (1996) Development 122, 881-894); (Yoshimizu et al., (1999) Dev. Growth Differ. 41, 675-684); (Szabo et al., (2002) Mech. Dev. 115, 157-160); were used as donors for peripheral blood cell transplantation (PBCT). Past studies have shown that endogenous Oct4 expression in adult animals is restricted to germ cells (Schöler et al., (1989); EMBO J. 8, 2543-2550); Yoshimizu et al., (1999), and the introduction of deletions in the proximal enhancer of the Oct4 promoter (ΔPE) leads to exclusive expression of the transgene in the germline even during embryogenesis (Yeom et al., 1996).

Peripheral blood was harvested from adult (7-10 weeks of age) transgenic female mice with Oct4-specific expression of GFP, or from adult male Oct4-GFP transgenic mice, and layered on Ficoll-Paque Plus (Amersham Biosciences/GE Healthcare, Piscataway, N.J.). The samples were centrifuged at 800×g for 15 min at 4 C, and mononuclear cells were collected from the Ficoll-buffer interface. The cells were then washed and resuspended in PBS at a final concentration of $2\text{-}4 \times 10^7$ cells/ml. In some experiments described below, recipient adult (6-7 weeks of age) wild-type or Atm-null female mice were conditioned with chemotherapy as described above for BMT, followed by PBCT (0.5 ml of cells per mouse, via the tail vein) 24 hr later. In all cases, ovaries were collected 28-30 hr after PBCT and analyzed for GFP expression by immunohistochemistry. For the experiments involving PBCT using males as donors, recipient ovaries were fixed, serially sectioned and screened in their entirety for GFP-expressing oocytes. As positive controls, testicular and ovarian tissues from Oct4-GFP (TgOG2) mice were analyzed in parallel to confirm transgene expression in males as well as antigen detection in ovaries.

As controls, GFP expression was detected only in primordial and growing oocytes of transgenic females (FIGS.

2A-2B), and the GFP signal was absent in oocytes of wild-type females prior to PBCT (FIG. 2C). However, primordial follicles with highly GFP-positive (GFP) oocytes were detected in the ovaries of chemo-ablated adult wild-type female mice within 28-30 hr of PBCT (FIGS. 2D-2F; see also FIG. 4).

Figures 3A, 3B, 3C:
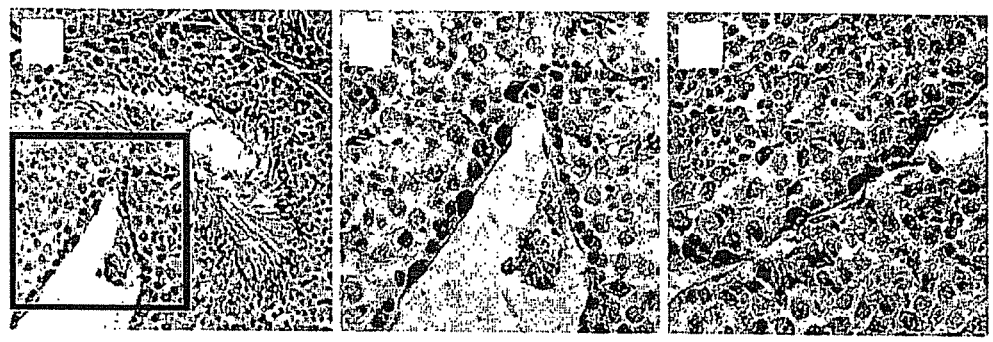
FIG. 3 shows results indicating that male peripheral blood does not generate oocytes in transplanted female mice. Immunohistochemical detection of GFP expression (brown, highlighted by arrowheads) in germ cells in the testes of adult TgOG2 male mice, confirming faithful and abundant expression of the transgene in males (A-C). Representative immunohistochemical analyses of ovaries of chemotherapy-treated adult female mice 28-30 hr following PBCT using adult male TgOG2 mice as donors, showing a lack of GFP signal in primordial oocytes (arrowheads) (D-E). Serially sectioned ovaries from three recipients were screened in their entirety, and no GFP-positive oocytes were observed in over 750 sections analyzed. In addition to the testicular samples shown above (A-C), ovaries from adult TgOG2 females were also run in parallel as a positive control for GFP detection in oocytes (data not shown, see FIG. 2).
Figures 3D, 3E, 3F:
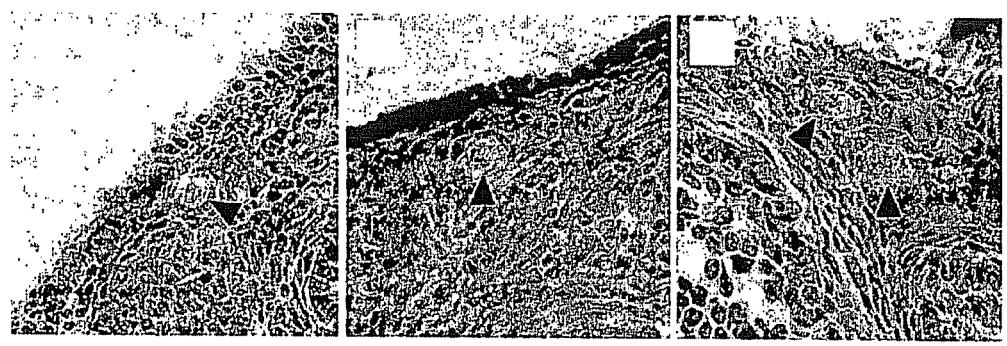
Figures 4J, 4K, 4L:
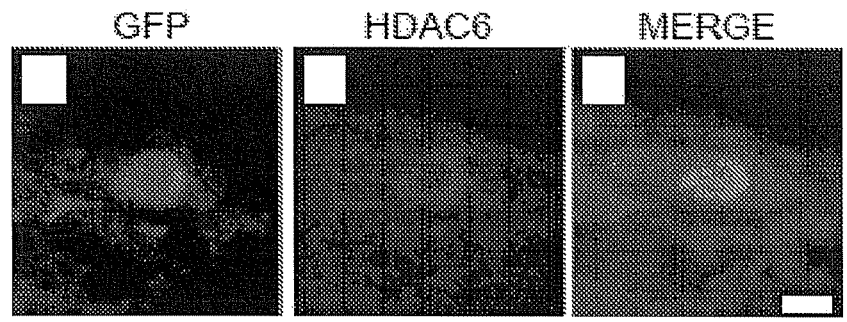
FIG. 4 depicts PBCT-derived ovarian follicular cells expressing germline and oocyte markers. Dual immunofluorescence analysis showing co-expression of GFP (green) and MVH (red) (A-F), GFP (green) and HDAC6 (red) (G-L), GFP (green) and NOBOX (red, note the nuclear localization) (M-0), or GFP (green) and GDF9 (red) (P-R), in oocytes of immature follicles within ovaries of recipient female mice 28-30 hr after transplantation with peripheral blood harvested from adult Oct4-GFP (TgOG2) transgenic females (see FIG. 2 for controls). In panels P and R, asterisks denote autofluorescent red blood cells. All cell nuclei are highlighted by TO-PRO-3 iodide staining (blue) in the merged panels. Scale bars=10 mm.
Figures 4M, 4N, 4O:
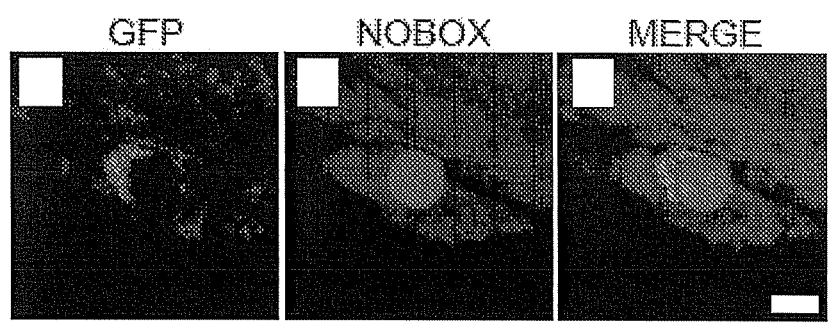
Figures 4P, 4Q, 4R:

Similar findings were obtained when the experiments were repeated using chemo-ablated Atm-null female mice as recipients (FIGS. 2G-2H), thus excluding the possibility of a non-specific 'restorative' effect of PBCT on endogenous oocyte production in the host females. Moreover, transplantation of peripheral blood-derived mononuclear cells harvested from adult male TgOG2 mice, which also exhibit abundant expression of the transgene in germ cells (FIGS. 3A-3C), did not result in the production of GFP$^+$ oocytes in chemotherapy-conditioned female recipients (FIGS. 3D-3F), ruling out the possibility that the oocytes observed following transplantation of female peripheral blood developed as a result of fusion between GFP-expressing donor cells and any residual host germ cells not destroyed by the chemo-ablation protocol.

The ability of peripheral blood derived female germline stem cells and their progenitors collected from Oct-4 GFP transgenic female donors to generate oocytes following transplantation into adult wildtype female mice was further evaluate by immunohistochemical analysis using antibodies specific for MVH (generously provided by T. Noce; Fujiwara et al., 1994), HDAC6 (2162; Cell Signaling Technology, Beverly, Mass.), NOBOX (A. Rajkovic; Suzumori et al., 2002), GDF-9 (AF739; R&D Systems, Minneapolis, Minn.) or GFP (sc-9996; Santa Cruz Biotechnology, Santa Cruz, Calif.) after high temperature antigen unmasking, as recommended by each supplier. For the PBCT studies involving transgenic mice with ubiquitous expression of GFP as donors, antigen detection was visualized after tyramide amplification (PerkinElmer, Boston, Mass.) due to the low basal level of GFP expression in primordial oocytes in this line of mice (unpublished findings). In those experiments using immunofluorescence-based antigen detection, the sections were mounted with propidium iodide (Vectashield; Vector Laboratories, Burlingame, Calif.) or TO-PRO-3 iodide (Molecular Probes, Eugene, Oreg.) to visualize nuclei, and images were captured using a Zeiss LSM 5 Pascal Confocal Microscope. GFP$^+$ cells contained within follicles of hosts following transplantation of peripheral blood collected from adult female TgOG2 mice expressed MVH (FIGS. 4A-4F), HDAC6 (FIGS. 4G-4L), NOBOX (FIGS. 4M-4O) and GDF9 (FIGS. 4P-4R), supporting their status as germ cells (MVH: Noce et al., 2001) and oocytes (HDAC6; NOBOX: Suzumori et al., 2002; GDF9: McGrath et al., 1995).

These findings, along with the expression of germline markers in peripheral blood (Example 2), indicate that adult female mice possess circulating germline stem cells that support new oocyte production.

Example 2

Expression of Female Germline Stem Cell Marker Genes in Peripheral Blood

Figure 5A:
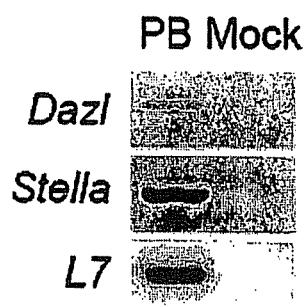
FIG. 5 depicts analysis of germline markers in peripheral blood of mice and humans. RT-PCR analysis of peripheral blood (PB) mononuclear cells isolated from adult female mice reveals expression of the germline markers, Dazi and Stella (L7, 'house-keeping' gene; Mock, mock reverse-transcribed RNA samples) (A). Data shown are representative of results obtained from analysis of 6 wild-type female mice between 7-10 weeks of age. Expression of DAZL and STELLA in peripheral blood mononuclear cells (PB) collected from 3 human female donors between 23-33 years of age (B). As a negative control, germline markers were not detected in two different adult human uterine (Ut) endometrial samples analyzed in parallel. GAPDH, amplified as an internal loading control. Mock, mock reverse-transcribed RNA samples.
Figure 5B:
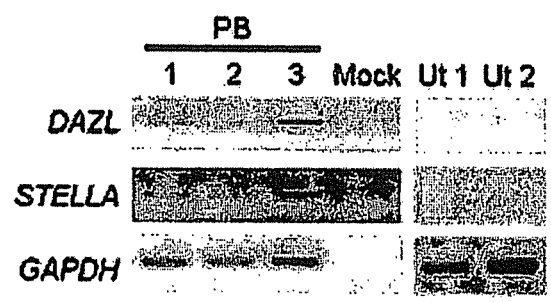

Expression of Dazl and Stella were detected in peripheral blood of mice and humans by RT-PCR (FIG. 5). Total RNA was extracted from each sample and 1 mg was reverse transcribed (Superscript II RT; Invitrogen, Carlsbad, Calif.) using oligo-dT primers. Amplification via 28-40 cycles of PCR was then performed using Taq polymerase and Buffer-D (Epicentre, Madison, Wis.) with primer sets specific for each gene (Supplemental Table S1). For each sample, RNA encoded by the ribosomal gene L7 (mouse studies), beta-actin (mouse studies) or the glyceraldehyde-3-phosphate dehydrogenase gene (GAPDH; human studies) was amplified and used as a loading control ('house-keeping' gene). All PCR products were isolated, subcloned and sequenced for confirmation.

Example 3

Female Germline Stem Cells in Peripheral Blood Derived from the Umbilical Cord

Figure 6:
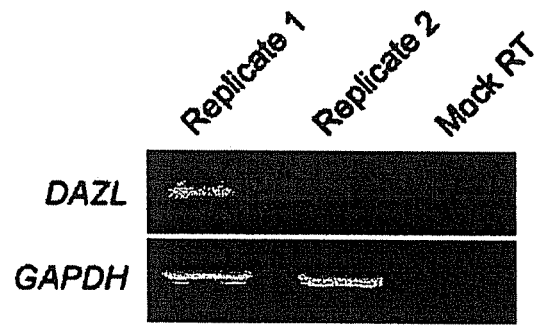
FIG. 6 depicts expression of Dazi in human umbilical cord blood, as detected by RT-PCR analysis.

Human cord blood was evaluated to determine whether cells that express the germ cell marker Dazl were present. Dazl has previously been detected in germ cells of both human fetal females (Brekhman et al., 2000 *Mol Hum Reprod* 6: 465-468; Tsai et al., 2000 *Fertil Steril* 73: 627-630) and human males (Brekhman et al., 2000 *Mol Hum Reprod* 6: 465-468). A single human cord blood sample was split into two replicate samples and RNA was extracted from each. The replicates were then reverse-transcribed, with mock-reverse transcribed negative control samples prepared in parallel. Samples were then used in polymerase chain reaction amplification reactions (RT-PCR) using primers specific for Dazl and the housekeeping gene GAPDH. As shown, the cord blood sample used is positive for Dazl in both replicates (FIG. 6). Human cord blood is therefore a novel source of germline stem cells, or their progenitors, for oocyte and sperm production in humans.

Example 4

Figure 7A:
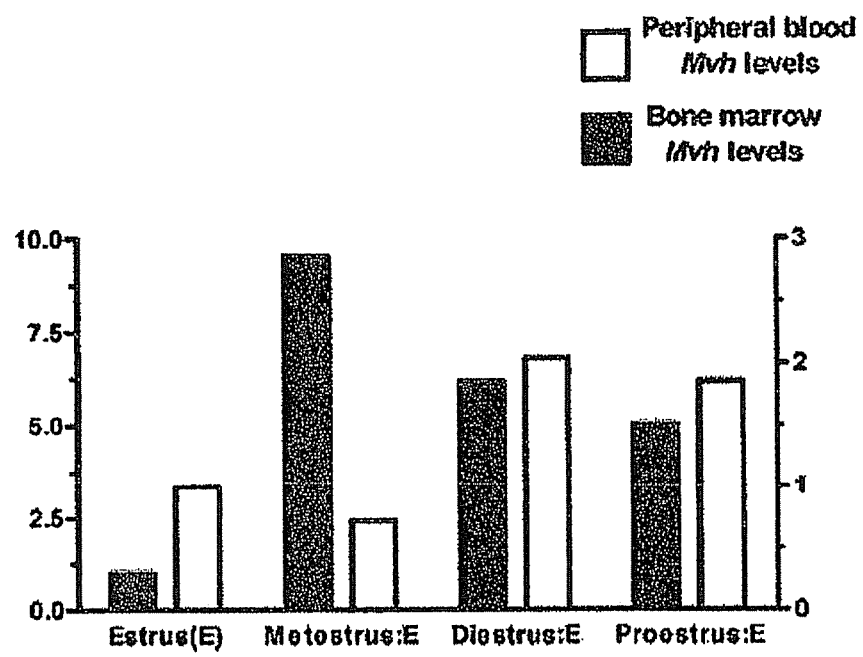
FIGS. 7A and B depicts real-time PCR analysis of Mvh levels in bone marrow or peripheral blood of adult female mice during the indicated stages of the estrous cycle. The data shown represent the combined results from an analysis of 3-4 mice per group, with mean levels at estrus set as the reference point for comparisons to other stages of the cycle following normalization against beta-actin for sample loading. For mice in estrus, Mvh expression in bone marrow was detected during linear amplification in only 1 of the 3 samples analyzed.
Figure 7B:
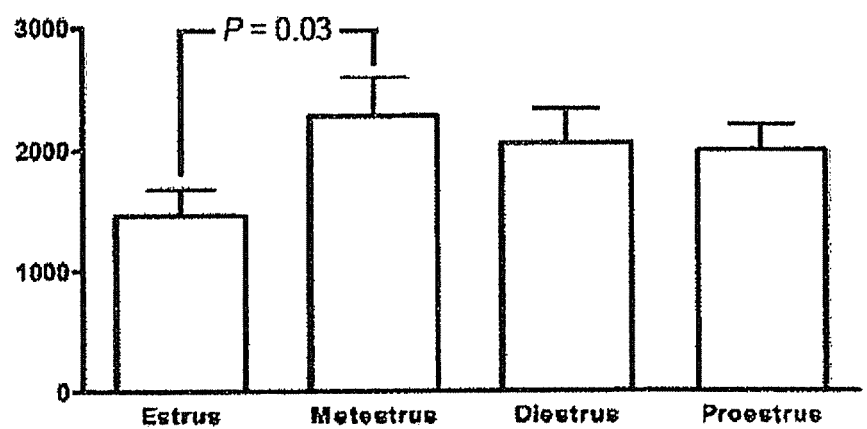

Modulation of Peripheral Blood Derived Female Germline Stem Cells and their Progenitors during the Estrous Cycle One aspect of the PBCT procedure that may impact the number of donor-derived oocytes generated is the stage of the donor female's reproductive cycle during which blood is harvested for transplantation. To begin testing whether the number of circulating genii cells fluctuates as a consequence of the estrous cycle, peripheral blood was collected from adult female mice during estrus, metestrus, diestrus and proestrus, and then analyzed by real-time PCR for Mvh expression. For quantitative analysis of Mvh levels, PCR was performed using a Cepheid Smart Cycler II and primers specific for amplification of Mvh (FAM-labeled LUX™ Fluorogenic Custom Primers, Invitrogen; forward (SEQ. ID NO: 1): cacctcagagggttttccaagcgaggg; reverse (SEQ ID NO: 2): cctct-tctgaacgggcctga and beta-actin (LUX™ Primer Sets for Housekeeping Genes IOIM-01; Invitrogen). Expression ratios were calculated using the method of Pfaffl (2001), with Mvh levels in bone marrow at estrus set as the reference point (1.0) for comparisons. The levels of this germline marker in peripheral blood were affected by the estrous cycle (FIG. 7). These results and those provided earlier in Examples 1-3 collectively indicate that adult female mice possess circulating germline stem cells, and their progenitor cells, that can generate oocytes, and suggest that the stage of the reproductive cycle during which blood is collected may impact the number of germline stem cells, and their progenitor cells, available for engraftment following transplantation.

References

Allen, E. (1923). Ovogenesis during sexual maturity. Am. J. Anat. 31, 439-470.

Attar, E. C., and Scadden, D. T. (2004). Regulation of hematopoietic stem cell growth. Leukemia 18, 1760-1768.

Barlow, C., Hirotsune, S., Paylor, R., Liyanage, M., Eckhaus, M., Collins, F., Shiloh, Y., Crawley, J. N., Ried, T., Tagle, D., and Wynshaw-Boris, A. (1996). Atm-deficient mice: a paradigm of ataxia telangiectasia. Cell 86, 159-171.

Barlow, C., Liyanage, M., Moens, P. B., Tarsounas, M., Nagashima, K., Brown, K., Rottinghaus, S., Jackson, S. P., Tagle, D., Ried, T., and Wynshaw-Boris, A. (1998). Atm deficiency results in severe meiotic disruption as early as leptonema of prophase I. Development 125, 4007-4017.

Benson, D. A., Karsch-Mizrachi, I., Lipman, D. J., Ostell, J., and Wheeler, D. L. (2004). GenBank: update. Nucleic Acids Res. 32 Database issue, D23-D26.

Bonadonna, G., and Valagussa, P. (1985). Adjuvant systemic therapy for resectable breast cancer. J. Clin. Oncol. 3, 259-275.

Borum, K. Oogenesis in the mouse. (1961). A study of meiotic prophase. Exp. Cell Res. 24, 495-507.

Braat, A. K., Zandbergen, T., van de Water, S., Goos, H. J., and Zivkovic, D. (1999). Charatcerization of zebrafish primordial germ cells: morphology and early distribution of vasa RNA. Dev. Dyn. 216, 153-167.

Brinster, C. J., Ryu, B. Y., Avarbock, M. R., Karagenc, L., Brinster, R. L., and Orwig, K. E. (2003). Restoration of fertility by germ cell transplantation requires effective recipient preparation. Biol. Reprod. 69, 412-420.

Brinster, R. L. (2002). Germline stem cell transplanation and transgenesis. Science 296, 2174-2176.

Bucci, L. R., and Meistrich, M. L. (1987). Effects of busulfan on murine spermatogenesis: cytotoxicity, sterility, sperm abnormalities, and dominant lethal mutations. Mutat. Res. 176, 259-268.

Calvi, L. M., Adams, G. B., Weibrecht, K. W., Weber, J. M., Olson, D. P., Knicht, M. C., Martin, R. P., Schipani, E., Divietti, P., Bringhurst, F. R., Milner, L. A., Kronenberg, H. M., and Scadden, D. T. (2003). Osteoblastic cells regulate the haematopoietic stem cell niche. Nature 425, 841-846.

Canning, J., Takai, Y., and Tilly, J. L. (2003). Evidence for genetic modifiers of ovarian follicular endowment and development from studies of five inbred mouse strains. Endocrinology 144, 9-12.

Capela, A., and Temple, S. (2002). LeX/ssea-1 is expressed by adult mouse CNS stem cells, identifying them as non-ependymal. Neuron 35, 865-875.

Castrillon, D. H., Quade, B. J., Wang, T. Y., Quigley, C., and Crum, C. P. (2000). The human VASA gene is specifically expressed in the germ cell lineage. Proc. Natl. Acad. Sci. USA 97, 9585-9590.

Cohen, P., and Pollard, J. W. (2001). Regulation of meiotic recombination and prophase I progression in mammals. BioEssays 23, 996-1009.

Cooke, H. J., Lee, M., Kerr, S., and Ruggiu, M. (1996). A murine homologue of the human DAZ gene is autosomal and expressed only in male and female gonads. Hum. Mol. Genet. 5, 513-516.

Cooper R. L., Goldman, J., and Vandenbergh, J. G. (1993). Monitoring of estrous cyclicity in the laboratory rodent by vaginal lavage. In Methods in Reproductive Toxicology, R. E. Chapin and J. J. Heindel, eds. (Orlando, Fla.: Academic Press), pp. 45-56.

Dearden, P., Grbic, M., and Donly, C. (2003). Vasa expression and germ-cell specification in the spider mite Tetranychus urticae. Dev. Genes Evol. 212, 599-603.

Deng, W., and Lin, H. (2001). Asymmetric germ cell division and oocyte determination during Drosophila oogenesis. Int. Rev. Cytol. 203, 93-138.

Dialynas, D. P., Quan, Z. S., Wall, K. A., Pierres, A., Quintans, J., Loken, M. R., Pierres, M., and Fitch, F. W. (1984). Characterization of the murine T cell surface molecule designated L3T4, identified by monoclonal antibody GK1.5: similarity of L3T4 to the human Leu 3/T4 molecule. J. Immunol. 131, 2445-2451.

Dias Neto, E., Correa, R. G., Verjovski-Almeida, S., Briones, M. R., Nagai, M. A., da Silva, W. Jr., Zago, M. A., Bordin, S., Costa, F. F., Goldman, G. H., Carvalho, A. F., Matsukuma, A., Baia, G. S., Simpson, D R., Brunstein, A., de Oliveira, P. S., Bucher, P., Jongeneel, C. V., O'Hare, M. J., Soares, F., Brentani, R. R., Reis, L. F., de Souza, S. J., and Simpson, A. J. (2000). Shotgun sequencing of the human transcriptome with ORF expressed sequence tags. Proc. Natl. Acad. Sci. USA 97, 3491-3496.

Di Giacomo, M., Barchi, M., Baudet, F., Edelman, W., Keeney, S., and Jasin, M. (2005). Distinct DNA-damage-dependent and -independent responses drive the loss of oocytes in recombination-defective mouse mutants. Proc. Natl. Acad. Sci. USA 102, 737-742.

Dong, J., Albertini, D. F., Nishimori, K., Kumar, T. R., Lu, N., and Matzuk, M. M. (1996). Growth differentiation factor-9 is required during early ovarian folliculogenesis. Nature 383, 531-535.

Erickson, G. F., and Shimasaki, S. (2000). The role of the oocyte in folliculogenesis. Trends Endocrinol. Metab. 11, 193-198.

Fabioux, C., Huvet, A., Lelong, C., Robert, R., Pouvereau, S., Daniel, J. Y., Minguant, C., Le Pennec, M. (2004). Oyster vasa-like gene as a marker of the germline cell development in Crassostrea gigas. Biochem. Biophys. Res. Commun. 320, 592-598.

Faddy, M. J., Gosden, R. G., Gougeon, A., Richardson, S. J., and Nelson, J. F. (1992). Accelerated disappearance of ovarian follicles in mid-life: implications for forecasting menopause. Hum. Reprod. 7, 1342-1346.

Fox, M., Damjanov, I., Martinez-Hernandez, A., Knowles, B. B., and Solter, D. (1981). Immunohistochemical localization of the early embryonic antigen (SSEA-1) in post-implantation mouse embryos and fetal and adult tissues. Dev. Biol. 83, 391-398.

Franchi, L. L., Mandl, A. M., and Zuckerman, S. (1962). The development of the ovary and the process of oogenesis. In The Ovary, S. Zuckerman, ed. (New York, N.Y.: Academic Press), pp. 1-88.

Fujiwara, Y., Komiya, T., Kawabata, H., Sato, M., Fujimoto, H., Furusawa, M., and Noce, T. (1994). Isolation of a DEAD-family protein gene that encodes a murine homolog of Drosophila vasa and its specific expression in germ cell lineage. Proc. Natl. Acad. Sci. USA 91, 12258-12262.

Geijsen, N., Horoschak, M., Kim, K., Gribnau, J., Eggan, K., and Daley, G. Q. (2004). Derivation of embryonic germ cells and male gametes from embryonic stem cells. Nature 427, 148-154.

Generoso, W. M., Stout, S. K. & Huff, S. W. (1971). Effects of alkylating agents on reproductive capacity of adult female mice. Mutat. Res. 13, 171-184.

Gilboa, L., and Lehmann, R. (2004). Repression of primordial germ cell differentiation parallels germ line stem cell maintenance. Curr. Biol. 14, 981-986.

Gosden, R. G. (1996). The vocabulary of the egg. Nature 383, 485-486.

Gosden, R. G. (2004). Germline stem cells in the postnatal ovary: is the ovary more like a testis? Hum. Reprod. Update 10, 193-195.

Gosden, R. G., Laing, S. C., Felicio, L. S., Nelson, J. F., and Finch, C. E. (1983). Imminent oocyte exhaustion and reduced follicular recruitment mark the transition to acyclicity in aging C57BL/6J mice. Biol. Reprod. 28, 255-260.

Green, E. L., and Bernstein, S. E. (1970). Do cells outside the testes participate in repopulating the germinal epithelium after irradiation? Negative results. Int. J. Radiat. Biol. Relat. Stud Phys. Chem. Med. 17, 87-92.

Grove, J. E., Bruscia, E., and Krause, D. S. (2004). Plasticity of bone marrow-derived stem cells. Stem Cells 22, 487-500.

Hadjantonakis, A. K., Gertsenstein, M., Ikawa, M., Okabe, M., and Nagy, A. (1998). Generating green fluorescent mice by germline transmission of green fluorescent ES cells. Mech. Dev. 76, 79-90.

Heike, T., and Nakahata, T. (2004). Stem cell plasticity in the hematopoietic system. Int. J. Hematol. 79, 7-14.

Hershlag, A., and Schuster, M. W. (2004). Return of fertility after autologous stem cell transplantation. Fertil. Steril. 77, 419-421.

Herzog, E. L., Chai, L., and Krause, D. S. (2003). Plasticity of marrow-derived stem cells. Blood 102, 3483-3493.

Hirshfield, A. N. (1991). Development of follicles in the mammalian ovary. Int. Rev. Cytol. 124, 43-101.

Ikenishi, K. (1998). Germ plasm in *Caenorhabditis elegans, Drosophila* and *Xenopus*. Der. Growth Differ. 40, 1-10.

Johnson, J., Canning, J., Kaneko, T., Pru, J. K., and Tilly, J. L. (2004). Germline stem cells and follicular renewal in the postnatal mammalian ovary. Nature 428, 145-150.

Kanatsu-Shinohara, M., Inoue, K., Lee, J., Yoshimoto, M., Ogonuki, N., Mild, H., Baba, S., Kato, T., Kazuki, Y., Toyokuni, S., Toyoshima, M., Niwa, O., Oshimura, M., Heike, T., Nakahata, T., Ishino, F., Ogura, A., and Shinohara, T. (2004). Generation of pluripotent stem cells from neonatal mouse testis. Cell 119, 1001-1012.

Komiya, T., Itoh, K., Ikenishi, K., and Furusawa, M. (1994). Isolation and characterization of a novel gene of the DEAD box protein family which is specifically expressed in germ cells of *Xenopus laevis*. Dev. Biol. 162, 354-363.

Lawson, K. A., and Hage, W. J. (1994). Clonal analysis of the origin of primordial germ cells in the mouse. Ciba Found. Symp. 182, 68-84, 84-91.

Lin, H. (2002). The stem-cell niche theory: lessons from flies. Nat. Rev. Genet. 3, 931-940.

Marani, E., van. Oers, J. W., Tetteroo, P. A., Poelmann, R. E., van der Veeken, J., and Deenen, M. G. (1986). Stage specific embryonic carbohydrate surface antigens of primordial germ cells in mouse embryos: FAL (S.S.E.A.-1) and globoside (S.S.E.A.-3). Acta Morphol. Neerl. Scand. 24, 103-110.

Matzuk, M. M., Burns, K. H., Viveiros, M. M., and Eppig, J. J. (2002). Intercellular communication in the mammalian ovary: oocytes carry the conversation. Science 296, 2178-2180.

McGrath, S. A., Esquela, A. F., and Lee, S. J. (1995). Oocyte-specific expression of growth/differentiation factor-9. Mol. Endocrinol. 9, 131-136.

McLaren, A. (1984). Meiosis and differentiation of mouse germ cells. Symp. Soc. Exp. Biol. 38, 7-23.

McLaren, A. (2003). Primordial germ cells in the mouse. Dev. Biol. 262, 1-15.

Medvinsky, A., and Dzierzak, E. (1996). Definitive hematopoiesis is autonomously initiated by the AGM region. Cell 86, 897-906.

Meirelles, L. da S., and Nardi, N. B. (2003). Murine marrow-derived mesenchymal stem cell: isolation, in vitro expansion, and characterization. Br. J. Haematol. 123, 702-711.

Milhem, M., Mahmud, N., Lavelle, D., Araki, H., DeSimone, J., Saunthararajah, Y, and Hoffman, R. (2004). Modification of hematopoietic stem cell fate by 5aza 2'deoxycytidine and trichostatin A. Blood 103, 4102-4110.

Mintz, B., and Russell, E. S. (1957). Gene-induced embryological modification of primordial germ cells in the mouse. J. Exp. Zool. 134, 207-230.

Molyneaux, K., and Wylie, C. (2004). Primordial germ cell migration. Int. J. Dev. Biol. 48, 537-544.

Morita, Y., Perez, G. I., Paris, F., Miranda, S., Ehleiter, D., Haimovitz-Friedman, A., Fuks, Z., Xie, Z., Reed, J. C., Schuchman, E. H., Kolesnick, R. N., and Tilly, J. L. (2000). Oocyte apoptosis is suppressed by disruption of the acid sphingomyelinase gene or by sphingosine-1-phosphate therapy. Nat. Med. 6, 1109-1114.

Morrison, S. J., Uchida, N., Weissman, I. L. (1995). The biology of hematopoietic stem cells. Annu. Rev. Cell Dev. Biol. 11, 35-71.

Noce, T., Okamoto-Ito, S., and Tsunekawa, N. (2001). Vasa homolog genes in mammalian germ cell development. Cell Struct. Funct. 26, 131-136.

Okada, S., Nakauchi, H., Nagayoshi, K., Nishikawa, S., Nishikawa, S., Miura, Y., and Suda, T. (1991). Enrichment and characterization of murine hematopoietic stem cells that express c-kit molecule. Blood 78, 1706-1712.

Okada, S., Nakauchi, H., Nagayoshi, K., Nishikawa, S., Miura, Y., and Suda, T. (1992). In vivo and in vitro stem cell function of c-kit- and Sca-1-positive murine hematopoietic cells. Blood 80, 3044-3050.

Perez, G. I., Knudson, C. M., Leykin, L., Korsmeyer, S. J. & Tilly, J. L. (1997). Apoptosis-associated signaling pathways are required for chemotherapy-mediated female germ cell destruction. Nat. Med. 3, 1228-1232.

Perez, G. I., Robles, R., Knudson, C. M., Flaws, J. A., Korsmeyer, S. J., and Tilly, J. L. (1999). Prolongation of ovarian lifespan into advanced chronological age by Bax-deficiency. Nat. Genet. 21, 200-203

Peters, H. (1969). The development of the mouse ovary from birth to maturity. Acta Endocrinol. 62, 98-116.

Peters, H. (1970). Migration of gonocytes into the mammalian gonad and their differentiation. Phil. Trans. Roy. Soc. Lond. B. 259, 91-101.

Philpott, C. C., Ringuette, M. J., and Dean, J. (1987). Oocyte-specific expression and developmental regulation of ZP3, the sperm receptor of the mouse zona pellucida. Dev. Biol. 121, 568-575.

Pfaffl, M. W. (2001). A new mathematical model for relative quantification in real-time RT-PCR. Nucleic Acids Res. 29, e45.

Rajkovic, A., Pangas, S. A., Ballow, D., Suzumori, N., and Matzuk, M. M. (2004). NOBOX deficiency disrupts early folliculogenesis and oocyte-specific gene expression. Science 305, 1157-1159.

Rich, I. N. (1995). Primordial germ cells are capable of producing cells of the hematopoietic system in vitro. Blood 86, 463-472.

Richardson, S. J., Senikas, V., and Nelson, J. F. (1987). Follicular depletion during the menopausal transition: evidence for accelerated loss and ultimate exhaustion. J. Clin. Endocrinol. Metab. 65, 1231-1237.

Rongo, C., Broihier, H. T., Moore, L., Van Doren, M., Forbes, A., and Lehmann, R. (1997). Germ plasm assembly and germ cell migration in *Drosophila*. Cold Spring Harb. Symp. Quant. Biol. 62, 1-11.

Roussell, D. L., and Bennett, K. L. (1993). glh-1, a germ-line putative RNA helicase from *Caenorhabditis*, has four zinc fingers. Proc. Natl. Acad. Sci. USA 90, 9300-9304.

Rya, B. Y., Orwig, K. E., Avarbock, M. R., and Brinster, R. L. (2003). Stem cell and niche development in the postnatal rat testis. Dev. Biol. 263, 253-263.

Saitou, M., Barton, S. C., and Surani, M. A. (2002). A molecular programme for the specification of germ cell fate in mice. Nature 418, 293-300.

Salooja, N., Chatterjee, R., McMillan, A. K., Kelsey, S. M., Newland, A. C., Milligan, D. W., Franklin, I. M., Hutchinson, R. M., Linch, D. C., and Goldstone, A. H. (1994). Successful pregnancies in women following single autotransplant for acute myeloid leukemia with a chemotherapy ablation protocol. Bone Marrow Transplant. 13, 431-435.

Salooja, N., Szydlo, R. M., Socie, G., R10, B., Chatterjee, R., Ljungman, P., Van Lint, M. T., Powles, R., Jackson, G., Hinterberger-Fischer, M., Kolb, H. J., and Apperley, J. F; Late Effects Working Party of the European Group for Blood and Marrow Transplantation. (2001). Pregnancy outcomes after peripheral blood or bone marrow transplantation: a retrospective study. Lancet 358, 271-276.

Salustri, A., Fulop, C., Camaioni, A., and Hascall, V. C. (2004). Oocyte-granulosa cell interactions. In The Ovary, 2nd Edition, P. C. K. Leung and E. Y. Adashi, eds. (San Diego: Elsevier Academic Press), pp. 131-143.

Samuelsson, A., Fuchs, T., Simonsson, B., and Bjorkholm, M. (1993). Successful pregnancy in a 28-year-old patient autografted for acute lymphoblastic leukemia following myeloablative treatment including total body irradiation. Bone Marrow Transplant. 12, 659-660.

Sanders, J. E., Hawley, J., Levy, W., Gooley, T., Buckner, C. D., Deeg, H. J., Doney, K., Storb, R., Sullivan, K., Witherspoon, R., and Appelbaum, F. R. (1996). Pregnancies following high-dose cyclophosphamide with or without high-dose busulfan or total-body irradiation and bone marrow transplantation. Blood 87, 3045-3052.

Sarmiento, M., Glasebrook, A. L., and Fitch, F. W. (1980). IgG or IgM monoclonal antibodies reactive with different determinants on the molecular complex bearing Lyt2 antigen block T cell-mediated cytolysis in the absence of complement. J. Immunol. 125, 2665-2672.

Schöller, H. R., Hatzopoulos, A. K., Balling, R., Suzuki, N., and Gruss, P. (1989). A family of octamer-specific proteins present during mouse embryogenesis: evidence for germline-specific expression of an Oct factor. EMBO J. 8, 2543-2550.

Sette, C., Dolci, S., Geremia, R., and Rossi, P. (2000). The role of stem cell factor and of alternative c-kit gene products in the establishment, maintenance and function of germ cells. Int. J. Dev. Biol. 44, 599-608.

Shen, H., Cheng, T., Olszak, I., Garcia-Zepeda, E., Lu, Z., Hellmann, S., Falon, R., Luster, A. D., and Scadden, D. T. (2001). CXCR-4 desensitization is associated with tissue localization of hematopoietic progenitor cells. J. Immunol. 166, 5027-5033.

Shiromizu, K., Thorgeirsson, S. S., and Mattison, D. R. (1984). Effect of cyclophosphamide on oocyte and follicle number in Sprague-Dawley rats, C57BL/6N and DBA/2N mice. Pediatr. Pharmacol. 4, 213-221.

Soyal, S. M., Amleh, A., and Dean. J. (2000). FIG□, a germ cell-specific transcription factor required for ovarian follicle formation. Development 127, 4645-4654.

Spangrude, G. J., and Scollay, R. (1990). A simplified method for enrichment of mouse hematopoietic stem cells. Exp. Hematol. 18, 920-926.

Spangrude, G. J., Heimfeld, S., and Weissman, I. L. (1988). Purification and characterization of mouse hematopoietic stem cells. Science 241, 58-62.

Spradling, A. C. (1993). Developmental genetics of oogenesis. In The Development of Drosophila melanogaster, Volume I, M. Bate and A. Martinez Arias, eds. (Cold Spring Harbor, N.Y.: Cold Spring Harbor Press), pp. 1-70.

Spradling, A. H., Drummond-Barbosa, D., and Kai, T. (2001). Stem cells find their niche. Nature 414, 98-104.

Su, A. I., Cooke, M. P., Ching, K. A., Hakak, Y., Walker, J. R., Wiltshire, T., Orth, A. P., Vega, R. G., Sapinoso, L. M., Moqrich, A., Patapoutian, A., Hampton, G. M., Schultz, P. G., and Hogenesch, J. B. (2004). A gene atlas of the mouse and human protein-encoding transcriptomes. Proc. Natl. Acad. Sci. USA 101, 6062-6067.

Suzumori, N., Yan, C., Matzuk, M. M., and Rajkovic, A. (2002). Nobox is a homeobox-encoding gene preferentially expressed in primordial and growing oocytes. Mech. Dev. 111, 137-141.

Szabo, P. E., Hübner, K., Schöler, H., and Mann, J. R. (2002). Allele-specific expression of imprinted genes in mouse migratory primordial germ cells. Mech. Dev. 115, 157-160.

te Velde, E. R., and Pearson, P. L. (2002). The variability of female reproductive ageing. Hum. Reprod. Update 8, 141-154.

Telfer, E. E. (2004). Germline stem cells in the postnatal mammalian ovary: a phenomenon of prosimian primates and mice? Reprod. Biol. Endocrinol. 2, 24.

Tilly, J. L. (2001). Commuting the death sentence: how oocytes strive to survive. Nat. Rev. Mol. Cell. Biol. 2, 838-848.

Tilly, J. L. (2003). Ovarian follicle counts—not as simple as 1, 2, 3. Reprod. Biol. Endocrinol. 1, 11.

Tropel, P., Noel, D., Platet, N., Legrand, P., Benabid, A.-L., and Berger, F. (2004). Isolation and characterisation of mesenchymal stem cells from adult mouse bone marrow. Exp. Cell Res. 295, 395-406.

Tsuda, M., Sasaoka, Y., Kiso, M., Abe, K., Haraguchi, S., Kobayashi, S., and Saga, Y. (2003). Conserved roles of nanos proteins in germ cell development. Science 301, 1239-1241.

Van de Rijn, M., Heimfeld, S., Spangrude, G. J., and Weissman, I. L. (1989). Mouse hematopoietic stem-cell antigen Sca-1 is a member of the Ly-6 antigen family. Proc. Natl. Acad. Sci. USA 86, 4634-4638.

van den Hurk, R., and Zhao, J. (2005). Formation of mammalian oocytes and their growth, differentiation and maturation within ovarian follicles. Theriogenology 63, 1717-1751.

Williams, D. E., de Vries, P., Namen, A. E., Widmer, M. B., and Lyman, S. D. (1992). The Steel factor. Dev. Biol. 151, 368-376.

Wognum, A. W., Eaves, A. C., and Thomas, T. E. (2003). Identification and isolation of hematopoietic stem cells. Arch. Med. Res. 34, 461-475.

Xu, Y., Ashley, T., Brainerd, E. E., Bronson, R. T., Meyn, M. S., and Baltimore, D. (1996). Targeted disruption of ATM leads to growth retardation, chromosomal fragmentation during meiosis, immune defects, and thymic lymphoma. Genes Dev. 10, 2411-2422.

Yeom, Y. I., Fuhrmann, G., Ovitt, C. E., Brehm, A., Ohbo, K., Gross, M., Hübner, K., and Schöler, H. R. (1996). Germline regulatory element of Oct-4 specific for the totipotent cycle of embryonal cells. Development 122, 881-894.

Yoshimizu, T., Sugiyama, N., De Felice, M., Yeom, Y. I., Ohbo, K., Masuko, K., Obinata, M., Abe, K., Schöler, H. R., and Matsui, Y. (1999). Germline-specific expression of the Oct-4/green fluorescent protein (GFP) transgene in mice. Dev. Growth Differ. 41, 675-684.

Yuan, L., Liu, J. G., Hoja, M. R., Wilbertz, J., Nordqvist, K., and Hoog, C. (2002). Female germ cell aneuploidy and embryo death in mice lacking the meiosis-specific protein SCP3. Science 296, 1115-1118.

Zhu, C. H., and Xie, T. (2003). Clonal expansion of ovarian germline stem cells during niche formation in *Drosophila*. Development 130, 2579-258.

Zuckerman, S. (1951). The number of oocytes in the mature ovary. Recent Prog. Horm. Res. 6, 63-108.

Zuckerman, S., and Baker, T. G. (1977). The development of the ovary and the process of oogenesis. In The Ovary, S. Zuckerman and B. J. Weir, eds. (New York, N.Y.: Academic Press), pp. 41-67.

3. The method of claim 1, wherein the sample is contacted with an antibody that binds to Vasa, a nucleic acid sequence that binds to Vasa mRNA or a combination thereof.

4. The method of claim 1, wherein determining the presence or absence of Vasa expression in step a) is carried out using a nucleic acid amplification method selected from the group consisting of rtPCR, ligase chain reaction, self sustained sequence replication, transcriptional amplification, Q-Beta Replicase and rolling circle replication.

5. The method of claim 3, wherein the antibody is anti-MVH.

6. The method of claim 1, wherein the female subject in need of in vitro fertilization is selected from a population of female subjects consisting of peri-menopausal subjects, post-menopausal subjects, subjects having gone through surgery, subjects having suffered from disease and subjects having suffered from ovarian damage.

7. The method of claim 6, wherein ovarian damage comprises damage caused by chemotherapy, radiotherapy or a combination of chemotherapy and radiotherapy.

8. The method of claim 7, wherein the radiotherapy is selected from the group consisting of ionizing radiation, ultraviolet radiation, X-rays and combinations thereof.

9. The method of claim 6, wherein the disease is selected from the group of reproductive disorders consisting of premature ovarian failure (POF), cancer, polycystic ovary disease, genetic disorders, immune disorders, metabolic disorders and combinations thereof.

10. The method of claim 9, wherein the reproductive disorder is POF.

11. A method of treating infertility in a female subject in need thereof, comprising:
    a) determining the presence or absence of Vasa expression in a sample of peripheral blood cells obtained from the female subject; and
    b) providing in vitro fertilization treatment to the female subject if Vasa expression is absent in the peripheral blood cells.

We claim:

1. A method of providing in vitro fertilization to a female subject in need thereof, said method comprising the steps of:
   a) determining the presence or absence of Vasa expression in a sample of peripheral blood obtained from the female subject, wherein the absence of Vasa expression corresponds to a loss of non-atretic follicles in the female subject compared to a female subject having a functional reproductive system; and
   b) providing in vitro fertilization to the female subject.

2. The method of claim 1, wherein the female subject is human.

* * * * *